United States Patent [19]
Laufer et al.

[11] Patent Number: 6,054,298
[45] Date of Patent: *Apr. 25, 2000

[54] FRINGE PROTEINS AND PATTERN FORMATION

[75] Inventors: Edward M. Laufer, Boston; Olivia E. Orozco, Arlington; Clifford J. Tabin, Cambridge, all of Mass.

[73] Assignee: President and Fellows of Harvard College, Cambridge, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/586,165

[22] Filed: Jan. 16, 1996

[51] Int. Cl.[7] .......................... C12P 21/00; C12N 15/63; C12N 15/85; C07H 21/04

[52] U.S. Cl. .................. 435/70.1; 435/320.1; 435/325; 435/410; 435/243; 536/23.4; 536/24.1

[58] Field of Search ............................ 435/252.3, 172.3, 435/6, 69.1, 70.1, 70.3, 71.1, 71.2, 320.1, 325, 377, 349, 243, 410; 800/2, DIG. 1, DIG. 2, DIG. 4; 536/23.5, 23.4, 24.1

[56] References Cited

PUBLICATIONS

A. Shatzman et al. Mech. Enzymol. 152:661–672.
Y.P. Yuan et al., "Secreted Fringe–like Signaling Molecules May be Glycosyltransferases", Cell 88 (1) :9–11 (1997).
C. Rodriguez–Esteban et al., "Radical fringe positions the apical ectodermal ridge at the dorsoventral boundary of the vertebrate limb", Nature 386 (27):360–366 (1997).
M.D. Adams et al., "Complementary DNA Sequencing: Expressed Sequence Tags and Human Genome Project", Science 252 (5013):1651–1656 (1991).
J.Y. Wu et al., "The Secreted Product of Xenopus Gene lunatic Fringe, a Vertebrate Signaling Molecule", Science 273 (5273):355–358 (1996).
Artavanis–Tsakonas, S., et al., "Notch Signaling", Science 268 :225–232 (1995).
Irvine, K.D. and Wieschaus, E., "fringe, a Boundary–Specific Signaling Molecule, Mediates Interactions between Dorsal and Ventral Cells during Drosophila Wing Development", Cell 79 :595–606 (1994).
Nye, J.S. and Kopan R., "Vertebrate ligands for Notch", Current Biology 5 (9):966–969 (1995).
Kim, J., et al., "Cell Recognition, Signal Induction, and Symmetrical Gene Activation at the Dorsal–Ventral Boundary of the Developing Drosophila Wing", Cell 82 :795–802 (1995).
Tax, F.E., et al., "Sequence of C. elegans lag–2 reveals a cell–signalling domain shared with Delta and Serrate of Drosophila", Nature 368 :150–154 (1994).

Primary Examiner—Brian R. Stanton
Assistant Examiner—Anne Marie S. Beckerleg
Attorney, Agent, or Firm—Hamilton, Brook, Smith & Reynolds, P.C.

[57] ABSTRACT

Isolated DNA encoding a protein or polypeptide having at least one biological activity of a vertebrate fringe protein, as well as the protein or polypeptide encoded thereby, are described. Assays for identifying agents which alter the expression of the described fringe genes and assays for agents which alter the production of angiogenic precursors, the formation of the apical ectodermal ridge and the subdivisions of the neural tube are also described.

4 Claims, 10 Drawing Sheets

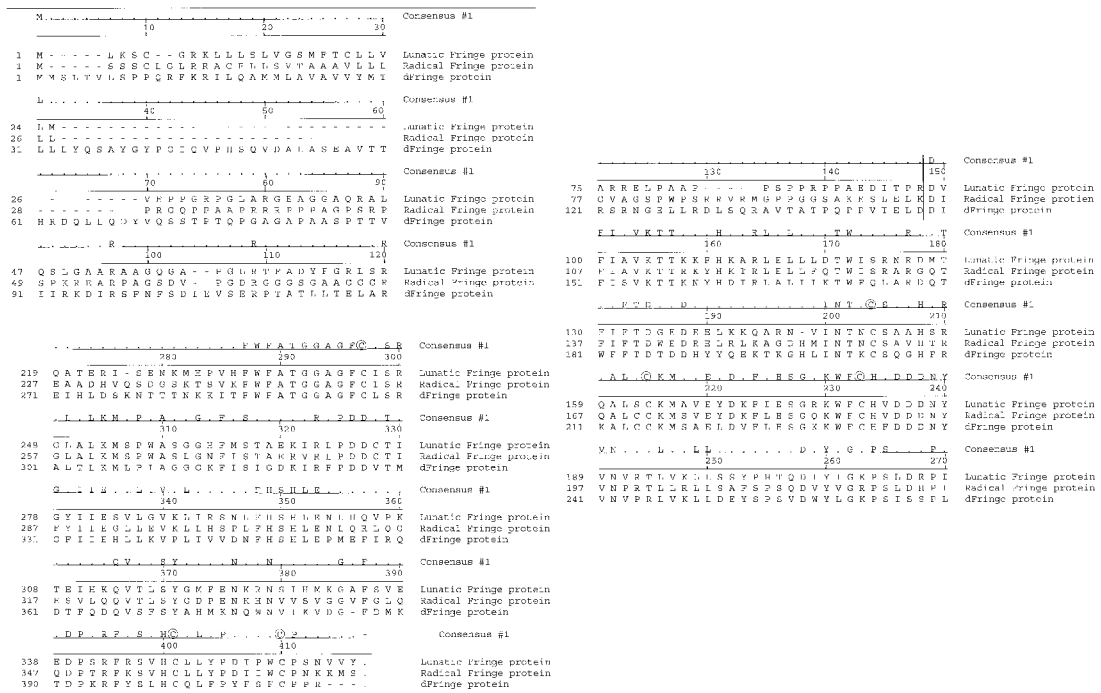

```
183/1                                    213/11
ATG AGC AGC TCC TGC CTG GGG CTC CGC AGA GCC TGC TTC CTG CTG TCC GTC ACC GCC GCC
 M   S   S   S   C   L   G   L   R   R   A   C   F   L   L   S   V   T   A   A
 *   A   A   P   A   W   G   S   A   E   P   A   S   C   C   P   S   P   P   P
     E   Q   L   L   P   G   A   P   Q   S   L   L   P   A   V   R   H   R   R
243/21                                   273/31
GCC GTT CTC CTG CTG CTG CTA GCC CCG GGG ACA GCC CCC CGC CGC GCC CCG CCG CCG CCC
 A   V   L   L   L   L   L   A   P   G   T   A   P   R   R   A   P   P   P   P
     P   F   S   C   C   C   S   P   R   G   Q   P   P   A   A   P   R   R   P
         R   S   P   A   A   A   R   P   G   D   S   P   P   P   R   P   A   A   A   R
303/41                                   333/51
GCC GCC CGC CGG GCC CAG CAG GCC CTC CCC GAA GCG GGA GGC GCG GCC CGC GGG GAG CGA
 A   A   R   R   A   Q   Q   A   L   P   E   A   G   G   A   A   R   G   E   R
     P   P   A   G   P   S   R   P   S   P   K   R   E   A   R   P   A   G   S   D
         R   P   P   G   P   A   G   P   P   R   S   G   R   R   G   P   R   G   A   T
363/61                                   393/71
CGT GCC CGG GGA CCG CGG CGG CGG CTC GGG AGC CGC GGG GGG CGG CCG GGG CGT CGC CGG
 R   A   G   P   R   R   R   L   G   S   R   G   G   R   P   G   R   R   R
     V   P   G   D   R   G   G   G   S   G   A   A   G   G   G   R   G   V   A   G
         C   P   G   T   A   A   A   A   R   E   P   R   G   A   A   G   A   S   P   V
423/81                                   453/91
TAG CCC GTG GCC TTC GCG GAG GGT CCG CAT GGG GCC TCC CGG CGG CTC GGC CAA GGA GAG
 *   P   V   A   F   A   E   G   P   H   G   A   S   R   R   L   G   Q   G   E
     S   P   W   P   S   R   R   V   R   M   G   P   P   G   G   S   A   K   E   S
         A   R   G   L   R   G   G   S   A   W   G   L   P   A   A   R   P   R   R   A
483/101                                  513/111
CCT GGA GCT AAA AGA CAT CTT TAT TGC GGT GAA AAC GAC GAG GAA GTA TCA CAA GAC GCG
 P   G   A   K   R   H   L   Y   C   G   E   N   D   E   E   V   S   Q   D   A
     L   E   L   K   D   I   F   I   A   V   K   T   T   R   K   Y   H   K   T   R
         W   S   *   K   T   S   L   L   R   *   K   R   R   G   S   I   T   R   R   G
543/121                                  573/131
GCT GGA GCT GCT GTT CCA AAC CTG GAT CTC CCG GGC GAG AGG ACA GAC ATT CAT ATT CAC
 A   G   A   A   V   P   N   L   D   L   P   G   E   R   T   D   I   H   I   H
     L   E   L   L   F   Q   T   W   I   S   R   A   R   G   Q   T   F   I   F   T
         W   S   C   C   S   K   P   G   S   P   G   R   E   D   R   H   S   Y   S   Q
603/141                                  633/151
AGA CTG GGA GGA TCG AGA GCT GCG CCT GAA AGC AGG GGA TCA TAT GAT CAA CAC TAA CTG
 R   L   G   G   S   R   A   A   P   E   S   R   G   S   Y   D   Q   H   *   L
     D   W   E   D   R   E   L   R   L   K   A   G   D   H   M   I   N   T   N   ©
         T   G   R   I   E   S   C   A   *   K   Q   G   I   I   *   S   T   L   T   V
663/161                                  693/171
TTC TGC TGT CCA CAC CCG GCA AGC TCT GTG CTG CAA GAT GTC TGT GGA ATA TGA TAA ATT
 F   C   C   P   H   P   A   S   S   V   L   Q   D   V   C   G   I   *   *   I
     S   A   V   H   T   R   Q   A   L   C   ©   K   M   S   V   E   Y   D   K   F
         L   L   S   T   P   G   K   L   C   A   A   R   C   L   W   N   M   I   N   S
723/181                                  753/191
CCT AGA ATC TGG ACA AAA GTG GTT TTG CCA TGT GGA CGA TGA CAA CTA TGT GAA TCC ACG
 P   R   I   W   T   K   V   V   L   P   C   G   R   *   Q   L   C   E   S   T
     L   E   S   G   Q   K   W   F   ©   H   V   D   D   D   N   Y   V   N   P   R
         *   N   L   D   K   S   G   F   A   M   W   T   M   T   T   M   *   I   H   G
783/201                                  813/211
GAC TCT CTT GCG TCT CTT ATC TGC CTT CTC ACC CAG CCA GGA TGT CTA TGT GGG ACG ACC
 D   S   L   A   S   L   I   C   L   L   T   Q   P   G   C   L   C   G   T   T
     T   L   L   R   L   L   S   A   F   S   P   S   Q   D   V   Y   V   G   R   P
         L   S   C   V   S   Y   L   P   S   H   P   A   R   M   S   M   W   D   D   R
```

FIG. 1A

```
843/221                                    873/231
GAG TCT GGA CCA TCC CAT TGA AGC AGC TGA CCA TGT CCA AAG CGA TGG ATC AAA GAC AAG
 E   S   G   P   S   H   *   S   S   *   P   C   P   K   R   W   I   K   D   K
  S   L   D   H   P   I   E   A   A   D   H   V   Q   S   D   G   S   K   T   S
   V   W   T   I   P   L   K   Q   L   T   M   S   K   A   M   D   Q   R   Q   A
903/241                                    933/251
CGT GAA ATT CTG GTT TGC CAC AGG TGG AGC AGG GTT CTG TAT CAG CAG AGG TCT TGC TCT
 R   E   I   L   V   C   H   R   W   S   R   V   L   Y   Q   Q   R   S   C   S
  V   K   F   W   F   A   T   G   G   A   G   F   ©   I   S   R   G   L   A   L
   *   N   S   G   L   P   Q   V   E   Q   G   S   V   S   A   E   V   L   L   *
963/261                                    993/271
GAA GAT GAG TCC CTG GGC AGG CCT GGG TAA TTT CAT CAG TAC TGC AGA AAG AGT GCG TCT
 E   D   E   S   L   G   Q   P   G   *   F   H   Q   Y   C   R   K   S   A   S
  K   M   S   P   W   A   S   L   G   N   F   I   S   T   A   E   R   V   R   L
   R   *   V   P   G   P   A   W   V   I   S   S   V   L   Q   K   E   C   V   F
1023/281                                   1053/291
TCC TGA TGA CTG CAC CAT TGG CTA CAT CAT TGA AGG CTG CTG GAA GTA AAG CTG CTG CA
 S   *   *   L   H   H   W   L   H   H   *   R   A   A   G   S   K   A   A
  P   D   D   C   T   I   G   Y   I   I   E   G   L   L   E   V   K   L   L   H
   L   M   T   A   P   L   A   T   S   L   K   G   C   W   K   *   S   C   C   T
1083/301                                   1113/311
CAG CCC ATT GTT CCA TTC CCA TCT GGA AAA TCT GCA GAG ACT ACA AGG AGA GTC TGT GCT
 Q   P   I   V   P   F   P   S   G   K   S   A   E   T   T   R   R   V   C   A
  S   P   L   F   H   S   H   L   E   N   L   Q   R   L   Q   G   E   S   V   L
   A   H   C   S   I   P   I   W   K   I   C   R   D   Y   K   E   S   L   C   C
1143/321                                   1173/331
GCA ACA GGT AAC CCT AAG TTA TGG GGA CCC TGA AGA ACA ACA ACA TGT TGT GAG TGT GGG
 A   T   G   N   P   K   L   W   G   P   *   E   Q   T   Q   C   C   E   C   G
  Q   Q   V   T   L   S   Y   G   D   P   E   N   K   H   N   V   V   S   V   G
   N   R   *   P   *   V   M   G   T   L   R   T   N   M   L   *   V   W   E
1203/341                                   1233/351
AGG AGT GTT TGG ACT TCA GCA AGA CCC AAC CAG ATT TAA ATC TGT CCA TTG TCT TCT TTA
 R   S   V   W   T   S   A   R   P   N   Q   I   *   I   C   P   L   S   S   L
  G   V   F   G   L   Q   Q   D   P   T   R   F   K   S   V   H   ©   L   L   Y
   E   C   L   D   F   S   K   T   Q   P   D   L   N   L   S   I   V   F   F   T
1263/361                                   1293/371
CCC TGA CAC TAT TTG GTG CCC AAT AAG AAA TGT CAT AA
 P   *   H   Y   L   V   P   Q   *   E   D   V   I
  P   D   T   I   W   ©   P   N   K   K   M   S   *
   L   T   L   F   G   A   P   I   R   R   C   H
```

FIG. 1B

```
  1 gtacatgggcggccgtggcggcggcggcgagcgcggggccgggccgcggcgcggaggtgcagcgaggaggaggagg ATG CTG AAG  77
                                                                              M   L   K    3
 78 AGC TGC GGG AGG AAG CTG CTC CTG TCC CTC GTG GGC TCC CTC ATG TTC ACC CTG GTG 137
  4  S   C   G   R   K   L   L   L   S   L   V   G   S   L   M   F   T   L   V   23
138 CTC ATG GTG GAG CCG CCG AGG GGC AGG CCG CTG GCT GAG GAG GCC GGT GGG GCT CAG 197
 24  L   M   V   E   P   P   R   G   R   P   L   A   E   E   A   G   G   A   Q   43
198 CGG GCG CTA CAG AGC CTG GGG CGG CCG CTG GGG GCG GCG CAG GGC GGC CTC CCG CGC 257
 44  R   A   L   Q   S   L   G   R   P   L   G   A   A   Q   G   G   L   P   R   63
258 ACG TTC GCC GAT TAC TTC GCC CGG CTG AGC GAG GCA CGC CGC CCC GCC CTG GCC CCG 317
 64  T   F   A   D   Y   F   A   R   L   S   E   A   R   R   P   A   L   A   P   83
318 CCG AGC CCC CGG CCA GCC GAG GAC ATC ACC CGG CTG GAG CTC CTC GAC GTC TTC ATC GTC 377
 84  P   S   P   R   P   A   E   D   I   T   R   L   E   L   L   D   V   F   I   A   V   103
378 AAA ACC AAG TTC CAC AAA GCG TTC ATC TTC ACG TGC TCG GCT GCA CAC AGC CGC TGG AGA AAG CAA 437
104  K   T   K   F   H   K   A   F   I   F   T   C   S   A   A   H   S   R   W   F   K   Q   123
438 CGC AAC CGC ATG ACC TTC ATC AAC ACC AAC GAT GAG GAT GAG CAC AGC GGG AGA AAG CTG TCC TGC 497
124  R   N   R   D   M   T   F   I   N   T   N   D   E   D   E   H   S   R   K   L   S   C   143
498 GCA CGA AAT GTC ATC GAG TAT GAC AAG TTC ATC GAG ACG CTG GTG AAG TGG TTC TGC CAT GTG 557
144  A   R   N   V   I   E   Y   D   K   F   I   E   S   L   V   K   W   F   C   H   V   163
558 AAG ATG GCT GTG GAG AAC TAC GTG AAC ACG CTG AAG CTC TCC AGC TAT CCC CAC 617
164  K   M   A   V   E   N   Y   V   N   T   L   V   K   L   L   S   S   Y   P   H   183
618 GAT GAT GAC AAC TAC GTG AAC GTG AGG ACG CTG CTG AGC CAG ATC CAG GAG AGG 677
184  D   D   D   N   Y   V   N   V   R   T   L   L   S   Q   I   Q   E   R   203
678 ACG CAG GAC ATC TAC ATC GGG AAG CCC AGC CTG GAC AGA CCC ATC CAG GCC ACA GAG AGG 737
204  T   Q   D   I   Y   I   G   K   P   S   L   D   R   P   I   Q   A   T   E   R   223
```

FIG. 2A

```
738  ATC AGC GAG AAC AAG ATG CAC CCT GTG CAT TTC TGG TTT GCC ACG GGA GGA GCA GGG TTT  797
224   I   S   E   N   K   M   H   P   V   H   F   W   F   A   T   G   G   A   G   F   243

798  TGT ATC AGC CGA GGG CTG GCG CTG AAG ATG AGC CCT TGG GCC AGT GCC GGT CAC TTC ATG  857
244   C   I   S   R   G   L   A   L   K   M   S   P   W   A   S   A   G   H   F   M   263

858  AGC ACC GCG GAG AAG ATC CGC CTG CCC GAT GAC TGC CTC TTC ATT GGC TAC ATC GAG TCC  917
264   S   T   A   E   K   I   R   L   P   D   D   C   L   F   I   G   Y   I   E   S   283

918  GTG CTG GGC GTG AAG CTT ATC CGC AGC AAC CTC TTC CAC TCT CAC TTG GAG AAC CTT CAC  977
284   V   L   G   V   K   L   I   R   S   N   L   F   H   S   H   L   E   N   L   H   303

978  CAG GTG CCC AAG ACA GAG ATC CAC ATG AAG CAG GTG ACA CTA AGC TAT GGC ATG TTT GAA AAC  1037
304   Q   V   P   K   T   E   I   H   M   K   Q   V   T   L   S   Y   G   M   F   E   N   323

1038 AAG CGC AAC TCC ATC CAC ATG AAG GGA GCC TTC TCC GTG GAG GAG GAC CCA TCC AGG TTT  1097
324   K   R   N   S   I   H   M   K   G   A   F   S   V   E   E   D   P   S   R   F   343

1098 CGC TCT GTG CAC TGC CTG CTG TAC CCC GAC ACG CCG TGG TGC CCT TCC AAC GTG GTG TAC  1157
344   R   S   V   H   C   L   L   Y   P   D   T   P   W   C   P   S   N   V   V   Y   363

1158 TAG gagacaagtgtccctcccaacctcgtcccgaatctcccggtatccgacgggtgtgcgggacctgctgctgtgca  1236
364   *                                                                              364

1237 ggtgtgtcggtcctccggacgaccctcgttgctgtggtattgcacagtgtgtgtactgaaggctgctgtgcggccctt  1316
1317 tgtcccctgccaccctgccctgctgggacgggagcgggtcctgagcacttaacccaggcatgggtga              1396
1397 gccctgcccgccgcagcccgccatgctgtgttgcctccccctccgaccccaactctaccctcttcctcttctctagctccca 1476
1477 ccagatgttggtttgttttttggtgtttgcctccttggtcaggtcacagtttacacactctcattcctccatggccacggcaaatg 1556
1557 aatctcagcatcgaggctccggtccttggtcaggtcacagtttacacactctcattcctccatggccacggcaaatg  1636
1637 caaagccagtgccagcattcgccaccattcccggagccccctacatcctgctgaaatgtttcagcggtgtaaatctat  1716
```

FIG. 2B

```
1717  gcactatttatagagaccaacttaaagactttctataatacggggagagagggaggagggctttccggagctgtgtg  1796
1797  tgcacagcgctgtggtgtctccccgttgtctccctgggctgagcacagacaccccacacccctgcacatagcgcttg  1876
1877  ggggagccttgtggctgtcccatctatgggctggaacatcctcctgcaggtgggtgctgtgggctggagcacc      1956
1957  tgggatgcttgtgtgtatgtggtgttcccaacctggcattgctctccggtgcaatgggagagtgatgggcacctaaaa  2036
2037  acacaggtgcccctcccaagcactgtcatcgttgtcccatcgctctcctggggaacctaagagtggatcccaccttcc  2116
2117  caggtacagctggagcaaaaccagtttgggaaacgctgcctgggagcaatgtttgccgtgagccaaggatgaatgtaacc  2196
2197  cattgcaacgagggttgggggactccgtgttccccatatccctctctcgtgtccctgtgggggggaccagcgggcagag  2276
2277  ctggagctgagcattccaaccgaagctgagtgaaaatggcccataatggtgcgttgtacatatgttattgcgccagt    2356
2357  attttttttactgtgcttttataacgttttctgcttttataaagaaaaaaaaacaacaagaaagctcaacatggagaattatgta  2436
2437  gatttaagatgctttttatacgttttctgtggatcggaaaagaagaaaaagacaaacgaccttctgataatctgtttaa  2516
2517  gaaagagaaaagagaaaaaattgcgttgtcttgtaactatcactaattatatgttccagtatctggaacgcc         2596
2597  actctgtgctttttgtaagtaggatgtgtctcgaggtgtagctgtgggatgggaactggggtgggcagtgcgttctc   2676
2677  agggacgtgaaccattcactgccaccgtccaccaataaagcagctttggctgaccccccgtcctgcaaaaaaaaaaa   2756
2757  aaaaaaaaaaaaa                                                                  2770
```

FIG. 2C

```
   1 ccggggcggc ttctcacgct agcggctcgg cccggagcgc cgggcgctgc cctccgccgg cccggggggc tccgccgcgt  80
  81 cccggagccg tctggtggag gccgcggggg aaaccgtccg cggggccatg ggggcctccc aggctggccg cgcagccgga 160
 161 cggggcccgg tgggcccgca acATGAGCAG CTCCTGCCTG GGACAGCCCC GGCTCCGCA GAGCCTGCTT CCTGCTGTCC GTCACCGCCG 240
 241 CGCCCGTTCT CCTGCTGCTG CTCGCCCCGG GGACAGCGGG CCGCCGCCGC GGGACCGCGG CCGCCGCCCG CCGGCCCCAG 320
 321 CAGGCCCCTC CCGAAGCGGG AGGCGTCGCC CCGGGGAGC GACGTGCCCG GGGACCGGGG ATGGGCCTC CCGGCGGCTC GGAGCCGCGG 400
 401 GGGGCGGCCG GGGCGTCGCC GGTAGCCCGT GCCTTTCGCG GAGGTCCGC ATGGGCCTC CCGGCGGCTC GGCCAAGGAG 480
 481 AGCCTGGAGC TAAAGACAT CTTTATTGCG GTGAAAACGA CGAGGAAGTA TCACAAGACG CGGCTGGAGC TGCTGTTCCA 560
 561 AACCTGGATC TCCCGGCGA GAGGACAGAC ATTCATATTC ACAGACTGGG AGGATCGAGA GCTGCGCCTG AAAGCAGGGG 640
 641 ATCATATGAT CAACACTAAC TGTTCTGCTG TCCACACCCG GCAAGCTCTG TGCTGCAAGA TGTCTGTGGA ATATGATAAA 720
 721 TTCCTAGAAT CTGGACAAAA GTGTTTTGC CATGTGGACG ATGACAACTA TGTGAATCCA CGGACTCTCT TGCGTCTCTT 800
 801 ATCTGCCTTC TCACCCAGCC AGGATGTCTA TGTGGGACGA CCGAGTCTGG ACCATCCCAT TGAAGCAGCT GACCATGTCC 880
 881 AAAGCGATGG ATCAAAGACA AGCGTGAAAT TCTGGTTTGC CACAGGTGGA GCAGGTTCT GTATCAGCAG AGTCTTGCT 960
 961 CTGAAGATGA GTCCCTGGGC CAGCCTGGGT AATTTCATCA AAGAGTGCGT CTTCCTGATG CTTCCTGAA ACTGCACCAT 1040
1041 TGGCTACATC ATTGAAGGGC TGCTGGAAGT AAAGCTGCTG CACAGCCCAT TGTTCCATTC CCATCTGAA AATCTGCAGA 1120
1121 GACTACAAGG AGAGTCTGTG CTGCAACAGG TAACCCTAAG CCTGAGAACA ACACACAATGT TGTGAGTGTG 1200
1201 GGAGGAGTGT TTGGACTTCA GCAAGACCCA ACCAGATTTA AATCTGTCA TTGTCTTCTT TACCCTGACA CTATTTGGTG 1280
1281 CCCCAATAAG AAGATGTCAT AActttgac cagtcattga caccttatc ctacctactt tgcgtaaagc aagagttgtg 1360
1361 atggctttt tttcttctg gacacaaaca gacatatcta caaagaggt agactttgta cagaagcaag actgctaat 1440
1441 tatgccaaga agcattgt tcagctgcag cctggacat tgccaagaag aaaatcttct atttcttgtt ctttgtcca 1520
1521 gtggctcttc atgtgatgc tccagtcata gctgtacaag tcacttatg ctttcatctg atgtcacatg agccctgcct 1600
1601 atcatgtgaa tctgcctca gatcatcct aggcaaatgc agtacttaga atgatggcat tcttactact gttagcagct 1680
1681 ttcagaggc attgtcttga agctgaat tgtaagacc ctgcagtccc catggtgatg aggggatga agttttgct 1760
1761 tgtctttt gcaaacagga cttaagaac tctgtggct gccatattat acctcctcca ccgtgagct gaaacacagt 1840
1841 ctgtttgtaa acaccagaag tccaggaatt gctagggtag acaagggtga aagcctttgt catgggaaaa acctgtgta 1920
1921 aggtaaact gactcaggac ctcttaccac tgccaagag ttgcttacag ggcacattct tcccagcagt ctttgtgtac ctcccatgga 2000
2001 ggtgattgtc agacttggca tatttgatac tgaatggcag tgctgttga ttatgatggt ggctgctag gtccaagact 2080
2081 attccctgg tatttgatat tttgccagac cgtttctcc tcgtttctct gttggtaa tgttttctcc ctctttccct cagcaggtta 2160
2161 tatgagctgg agcatgccca ttgctgatg aaacccctg tagtataatt gtgaagc tgtctgtat ccttcactgc cagcaggtta 2240
2241 ggaggagtgg agcatagtg tatcatgtg aaggtttg tggtgctagt tcaaagtatg ttctgtcat cttgtgtgt ctgtggtttg 2320
2321 cccacacttca gcttcttaat gtaatcttt gagaccagtg tttatttta ctctacatct aatgtttcca gaagtaatt 2400
2401 ctgcacttg gtaaaggaa actgatgct gataacaaaa caggagtcca acgctgtagc aatgtcaccct gctgcgcatt 2480
2481 ataaattaaa taagcttagt gtttgaaagt gaagaattga catacaaaat gactctctat gtttagtttt gttacttcca actttgcctt 2560
2561 tgtcaatct atacctgatg tgaagaacag ggctgaatta tgggagaat aaccactgtt tactctcaaa ctcttcagaa 2640
2641 aatacttgca ggttagtac tagagcttgg tcagatttct agtgagcggtg agcatgatgt tgtataacct gaaactatga 2720
2721 ctaatggcga gaattcggac cgagcaagtt tcagatttct atcagctgtg ctgagcggtg tatttcagct agttgcttaa 2800
```

FIG. 3A

```
2801 cttcttccca tttgaaaagt ggtaccatgt aggcaaacac ctgcagcata ttcaagtatg aagtgcagtg taggtgtcag 2880
2881 cctcctgtaa tataatattc tctgctttct gttttgaag caaacctttc aacaactgga tacgttgtcc tctttgcatg 2960
2961 atttaattta atttataga ggagcaaaca agctgactac tcgctacgat ccagcagctt gttcttaaat ttctttttcct 3040
3041 ttatctgcta aggcagtgct ttgaccatga ggcacaggaa taagagtgct gcaagcactc ggatcaaagt ccacctagca 3120
3121 cagtggttgt ttcaaaacag gaacatctgt gatgctgaca gcctgttaca gagcgtggag ggctcgtggc agggtaggtg 3200
3201 gtgggatgtt ctacctctcc atcaggtggt ctgctcaata gaactgagat gtcctgtggt tcagtgatac gtcattcata 3280
3281 gctctggaga ttactggtat ctatataaac actttttaaa aaacatttgg tgggttcttg ttttcagcct ccttgtagca 3360
3361 aggagttgtg aagctgcata agcacttgat gagatatcat cctcagtgat ctctgaattc tgctggagct ttcttcctc 3440
3441 tcctcttaag agcagcctcc tgtcagatac tatggacagc acaagctggg tagtgattat gtggcaaact gcagttcaaa 3520
3521 gatgacaaca cttcatactg atggcagcaa aactgcgtag aagtcccata ctacagtcat ttcccaccct aatggagtt 3600
3601 tgctgcctcc ttgtcatgcc taatgctggt agggtgctta tcaagctgaa aaaggaacgt attcttctgt aaagcaatgc 3680
3681 aaaaaagctt ctttaaggtt tctcttgttc acaatacagt aggctctgta catatactga gatgcagctt cttaaactac 3760
3761 tgtcccatac gtaaaacaat tctatgaaat aaatatttaa gtatgtcaaa acctggtacc cggatcctcg attcctgcag 3840
3841 cccgggggat ccactagttc tagagcggcc gccaccggtg gagctccagc ttttgttccc tttagtgagg gttaatttcg 3920
3921 agcttggcgt aatcatg                                                                      3937
       |         |         |         |         |         |         |         |
       10        20        30        40        50        60        70        80
```

FIG. 3B

```
                                                                    Consensus #1
       M . . . . . . . . . . . . . . . . . . . . . . . . . . . . . .
  1    M - - - - - L K S C - - G R K L L L S L V G S M F T C L L V    Lunatic Fringe protein
  1    M - - - - - S S S C L G L R R A C F L L S V T A A A V L L L    Radical Fringe protein
  1    M M S L T V L S P P Q R F K R I L Q A M M L A V A V V Y M T    dFringe protein
                          10              20              30

Consensus #1
       L . . . . . . . . . . . . . . . . . . . . . . . . . . . . . .
 24    L M - - - - - - - - - - - - - - - - - - - - - - - - - - - -    Lunatic Fringe protein
 26    L L - - - - - - - - - - - - - - - - - - - - - - - - - - - -    Radical Fringe protein
 31    L L L Y Q S A Y G Y P P G I Q V P H S Q V D A L A S E A V T T    dFringe protein
                          40              50              60

Consensus #1
       . . . . . . . . . . . . . . . . . . . . . . . . . . . . . . .
 26    - - - - - - - - - V E P P G R P G L A R G E A G G A Q R A L    Lunatic Fringe protein
 28    - - - - - - - - - P R G Q P P A A P R R R P P P A G P S R P    Radical Fringe protein
 61    H R D Q L L Q D Y V Q S S T P T Q P G A G A P A A S P T T V    dFringe protein
                          70              80              90

R           Consensus #1
       . . . . . . . . . R . . . . . . . . . . . . . . . . . . . . .
 47    Q S L G A A R A A G Q G A - - P G L R T F A D Y F G R L S R    Lunatic Fringe protein
 49    S P K R E A R P A G S D V - - P G D R G G S G A A G G G R    Radical Fringe protein
 91    I I R K D I R S F N F S D I E V S E R P T A T L L T E L A R    dFringe protein
                          100             110             120
```

| | | | | | | |
|---|---|---|---|---|---|---|
| | . . . . \| . . . . \| . . . . \| . . . . \| . . . . \| . . . . \| | | | | | |
| | | | D | | | Consensus #1 |
| | | 130 | 140 | 150 | | |
| 75 | A R R E L P A A P | - - - P S P P R P P A E D I T P R D V | | | | Lunatic Fringe protein |
| 77 | G V A G S P W P S R | R V R M G P P G G S A K E S L E L K D I | | | | Radical Fringe protien |
| 121 | R S R N G E L L R D L | S Q R A V T A T P Q P P V T E L D D I | | | | dFringe protein |

| | | | | | | |
|---|---|---|---|---|---|---|
| | | | T | | R . | Consensus #1 |
| | | 160 | 170 | 180 | | |
| | F I . V K T T . | H . . R L . . . . . L . . . . T M . . . R . . . | | | | |
| 100 | F I A V K T T K K F | H K A R L E L L L D T W I S R N R D M T | | | | Lunatic Fringe protein |
| 107 | F I A V K T T R K Y | H K T R L E L L F Q T W I S R A R G Q T | | | | Radical Fringe protein |
| 151 | F I S V K T T K N Y | H D T R L A L I I K T W F Q L A R D Q T | | | | dFringe protein |

| | | | | | | |
|---|---|---|---|---|---|---|
| | | | | | H . R | Consensus #1 |
| | | 190 | 200 | 210 | | |
| | . F T D . . . D . . . . . . . . . . . . . . . . . . . I N T . C . S . . . | | | | | |
| 130 | F I F T D G E D E E | L K K Q A R N - V I N T N C S A A H S R | | | | Lunatic Fringe protein |
| 137 | F I F T D W E D R E | L R L K A G D H M I N T N C S A V H T R | | | | Radical Fringe protein |
| 181 | W F F T D D D H Y Y | Q E K T K G H L I N T K C S Q G H F R | | | | dFringe protein |

| | | | | | | |
|---|---|---|---|---|---|---|
| | | | | | D D D N Y | Consensus #1 |
| | | 220 | 230 | 240 | | |
| | . A L . C K M . . . | . E . D . F . E S G . K W F C H . D D D N Y | | | | |
| 159 | Q A L S C K M A V E | Y D K F I E S G R K K W F C H V D D D N Y | | | | Lunatic Fringe protein |
| 167 | Q A L C C K M S V E | Y D K F L E S G Q K W F C H V D D D N Y | | | | Radical Fringe protein |
| 211 | K A L C C K M S A E | L D V F L E S G K K W F C H F D D D N Y | | | | dFringe protein |

| | | | | | | |
|---|---|---|---|---|---|---|
| | | | | | P | Consensus #1 |
| | | 250 | 260 | 270 | | |
| | V N . . . . L . . . L L . . . . . . . . . D . Y . G . P S . . . | | | | | |
| 189 | V N V R T L V K L L | S S Y P H T Q D I Y I G K P S L D R P I | | | | Lunatic Fringe protein |
| 197 | V N P R T L L R L L | S A F S P S Q D V Y V G R P S L D H P I | | | | Radical Fringe protein |
| 241 | V N V P R L V K L L | D E Y S P S V D W Y L G K P S I S S P L | | | | dFringe protein |

```
                    .         .         .         .         .         .   
                    .         .         .         .         .         .   
                    .         .         . F W F A T G G A G F(C). S R         Consensus #1
    219  Q A T E R I - S E N K M H P V H F W F A T G G A G F C I S R         Lunatic Fringe protein
    227  E A A D H V Q S D G S K T S V K F W F A T G G A G F C I S R         Radical Fringe protein
    271  E I H L D S K N T T T N K K I T F W F A T G G A G F C L S R         dFringe protein
                    280       290       300

. L . L K M . P . A . G . F . S .         . R . P D D . T .         Consensus #1
    248  G L A L K M S P W A S G G H F M S T A E K I R L P D D C T I         Lunatic Fringe protein
    257  G L A L K M S P W A S L G N F I S T A E R V R L P D D C T I         Radical Fringe protein
    301  A L T L K M L P I A G G G K F I S I G D K I R F P D D V T M         dFringe protein
                    310       320       330

G . I I E . L . L . V . L .         . F H S H L E .         . G . F .     Consensus #1
    278  G Y I I E S V L G V K L I R S N L F H S H L E N L H Q V P K         Lunatic Fringe protein
    287  F Y I I E G L L E V K L L H S P L F H S H L E N L Q R L Q G         Radical Fringe protein
    331  G F I I E H L L K V P L T V V D N F H S H L E P M E F I R Q         dFringe protein
                    340       350       360

. Q V . S Y . . . N . . . . . G . . . F .                         Consensus #1
    308  T E I H K Q V T L S Y G M F E N K R N S I H M K G A F S V E         Lunatic Fringe protein
    317  E S V L Q Q V T L S Y G D P P E N K K H N V V S V G G V F G L Q     Radical Fringe protein
    361  D T F Q D Q V S F S Y A H M K N Q W N N V I K V D G - F D M K     dFringe protein
                    370       380       390

. D P . R F . S . . H(C). . L . P .         . .(C)P . .               Consensus #1
    338  E D P S R F K S V H C L L Y P D T P W C P S N V V Y . .              Lunatic Fringe protein
    347  Q D P T R F K S V H C L L Y P D T I W C P N K K M S . .              Radical Fringe protein
    390  T D P K R F Y S L H C Q L F P P Y F S F C P P P R - -                dFringe protein
```

FRINGE PROTEINS AND PATTERN FORMATION

GOVERNMENT SUPPORT

Work described herein was supported by grant R01 HD/GM32443 from the National Institute of Health and funding from the Howard Hughes Medical Institute. The U.S. government has certain rights in the invention.

BACKGROUND OF THE INVENTION

Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development, from the earliest establishment of the body plan, to the patterning of the organ systems, to the generation of diverse cell types during tissue differentiation (Davidson, *Development* 108:365–389 (1990); Gurdon, *Cell* 68:185–199 (1992); Jessell et al., *Cell* 68:257–270 (1992)).

The effects of developmental cell interactions are varied. Typically, responding cells are diverted from one route of cell differentiation to another by inducing cells which differ from both the uninduced and induced states of the responding cells. Sometimes cells induce their neighbors to differentiate like themselves (homogenetic induction); in other cases a cell inhibits its neighbors from differentiating like itself. Cell interaction in early development may be sequential, such that an initial induction between two cell types leads to a progressive amplification of diversity. Moreover, inductive interactions occur not only in embryos, but also in adult cells, and can act to establish and maintain morphogenetic patterns as well as induce differentiation (Gurdon (1992)). These interactions are thought to explain how distinct cell types emerge from a group of cells that have otherwise equivalent potentials.

Genetic and biochemical studies in invertebrates have shown that one means by which a signal may be transmitted is via the Notch/Lin-12/Glp-1 family of transmembrane proteins (Artavnis-Tsakonas et al., *Science* 268:225–232 (1995)). These proteins are thought to serve as receptors which are activated upon binding a member of the emerging DSL (Delta-Serrate-Lag-2) family of putative ligands (Tax et al., *Nature* 368:150–154 (1994)). Members of the DSL family are also transmembrane proteins, and activation of the receptor appears to require contact with an adjacent cell.

Three highly conserved vertebrate Notch receptor family members have also been identified, each of which is widely expressed during embryogenesis (Artavnis-Tsakonas et al., 1995). Additionally, vertebrate members of the DSL family have recently been identified (Henrique et al., *Cell* 80:909–918 (1995); Henrique et al., *Nature* 375:787–790 (1995); Chitnis et al., *Nature* 375:761–766 (1995); and Bettenhausen et al., *Development* (1995, in press)), fueling the speculation that the process of lateral cell signaling occurs in vertebrates in a manner similar to invertebrates. However, the molecular signals which regulate the cell interactions, signalling and pattern formation in this pathway and others are currently not well understood.

SUMMARY OF THE INVENTION

The present invention pertains to isolated DNA encoding a polypeptide having at least one biological activity of a vertebrate fringe protein, as well as to the polypeptide or protein encoded thereby. In one embodiment, the present invention pertains to isolated DNA encoding the fringe A (radical fringe) and fringe B (lunatic fringe) proteins and comprising the nucleic acid sequences of SEQ ID NOS: 1 and 6, respectively (FIGS. 1A–B and 2A–B, respectively). The present invention also pertains to the isolated fringe A protein comprising the amino acid sequence of SEQ ID NO: 5 (FIGS. 1A–B) and the isolated fringe B protein comprising the amino acid sequence of SEQ ID NO: 7 (FIGS. 2A–B). In an alternate embodiment, the nucleic acid sequence of the isolated DNA encoding a polypeptide having at least one biological activity of a vertebrate fringe protein is at least 30 percent identical to the nucleic acid sequence of either SEQ ID NOS: 1 or 6. In another embodiment, the amino acid sequence of the subject fringe proteins is at least 30 percent similar to the carboxy-terminal 60–75% of the amino acid sequence of either SEQ ID NOS: 5 or 7.

The present invention also makes available isolated proteins which are encoded by genes derived from vertebrate organisms, and which are capable of functioning either as an agonist of at least one biological activity of the described vertebrate fringe proteins or an antagonist of at least one biological activity of the described fringe proteins.

Exemplary biological activity which the present vertebrate fringe A protein may have includes the ability to affect neural-specification of cell type identity, proliferative regulation of migratory paths, proliferation of neural crest (branchial arches), definition of morphological boundaries, including limb specification of morphological boundaries, cell shape decisions and indirect regulation of proliferative signals.

Exemplary biological activity which the present vertebrate fringe B protein may have includes the ability to affect proliferative and fate specification signals of neural tissues, regulation of formation of components of ear, nose and facial structures, induction, patterning and proliferation of vasculature, and fate specification within somitic tissues.

Another aspect of the present invention relates to a method of inducing and/or maintaining a differentiated state of a cell responsive to a fringe protein, by contacting the cell with a fringe protein or a fringe agonist. For instance, it is contemplated by the invention that, in light of the present finding of a broad involvement of fringe proteins in the formation of ordered spatial arrangements of differentiated tissues in vertebrates, the subject method could be used to generate and/or maintain an array of different vertebrate tissues both in vitro and in vivo. The subject method can be practiced with, for example, the goal of inducing vasculature differentiation.

Another embodiment of the invention relates to a method of reducing or decreasing a differentiated state of a cell responsive to a fringe protein, by contacting the cells with a fringe antagonist. For example, the method of the present invention can be practiced with the goal of preventing or altering the subdivision of the neural tube in order to determine the effects of altered neural tube development on the development of the embryo.

The present invention also relates to an assay for identifying agents which alter the differentiation or. development of an organism. For example, an organism can be treated with the agent to be tested, and the expression pattern of the fringe A and/or fringe B genes can be assessed and compared with their respective expression patterns in a control organism in the absence of the agent to be tested. An increase in the expression of a particular fringe gene indicates that the agent is an agonist of at least one biological activity of, or has a positive effect on the expression of, that fringe gene. Similarly, a decrease in the expression of the fringe gene indicates that the agent is an antagonist of at least one biological activity of, or has a negative effect on, that fringe gene.

Alternatively, a similar assay is provided for identifying an agent which alters the formation of angiogenic precursors or angiogenic cells. For example, an agent to be tested can be administered to an organism, and the expression of fringe B in the test organism can be assessed in tissue or cells in which angiogenic precursors are formed, and the expression can be compared with the expression of fringe B in a control organism in the absence of the agent to be tested. A difference in the expression of fringe B indicates that the agent alters the formation of angiogenic precursors or angiogenic cells. The same assay can be used to identify agents which alter the formation of the apical ectodermal ridge (AER) by assessing the expression of fringe A in place of fringe B. The same assay can also be used to identify agents which alter the formation or subdivision of the neural tube by assessing the expression of fringe A and/or fringe B.

BRIEF DESCRIPTION OF THE DRAWINGS

FIGS. 1A–1B represent the partial nucleic acid sequence (SEQ ID NO: 1) of the chicken fringe A (radical fringe) gene and the three potential encoded amino acid sequences (SEQ ID NOS: 2, 3 and 4, respectively). There is a frame shift in the open reading frame between amino acids 27 and 28 (indicated with an X); as a result, the encoded protein includes part of SEQ ID NO: 2 (up to and including amino acid number 27) and part of SEQ ID NO: 3 (from amino acid 28 on). The complete sequence of the encoded protein is underlined (SEQ ID NO: 5). Conserved cysteine residues are indicated with circles at amino acid positions 160, 171, 189, 253, 357 and 366.

FIGS. 2A–C represent the nucleic acid sequence (SEQ ID NO: 6) and the translated amino acid sequence (SEQ ID NO: 7) of the chicken fringe B (lunatic fringe) gene. The coding region is indicated with capital letters, and conserved cysteine residues are indicated with circles at amino acid positions 152, 163, 181, 244, 348 and 359.

FIGS. 3A–3B represent the cDNA sequence (SEQ ID NO: 8) of chicken fringe A (radical fringe). The coding region is indicated with capital letters. There may also be an additional nucleotide between nucleotide positions 41 and 42 (indicated with an arrow).

FIGS. 4A–4C are an illustration of the amino acid residues which are conserved between the amino acid sequences of the fringe A (radical fringe) protein, the fringe B (lunatic fringe) protein and the Drosophila fringe (dFringe) protein (SEQ ID NO: 9). The consensus amino acid sequence is indicated above the alignment of the three fringe sequences, and the beginning of the conserved region is indicated with a vertical line between amino acid residues 148 and 149 of the consensus sequence.

DETAILED DESCRIPTION OF THE INVENTION

Three highly conserved vertebrate Notch family members have been identified, each of which is widely expressed during embryogenesis (Artavnis-Tsakonas et al., 1995). Additionally, vertebrate members of the DSL (Delta-Serrate-Lag-2) family have recently been identified (Henrique et al., (1995); Chitnis et al., (1995); and Bettenhausen et al., (1995)), fueling the speculation that the process of lateral cell signaling occurs in vertebrates in a manner similar to invertebrates. The vertebrate DSL family of transmembrane proteins has at least six members falling into two structural classes bearing homology to either Delta or Serrate, the two identified ligands for Notch in Drosophila (Nye and Kopan, Current Biology 5(9):966–969 (1995)). A homolog of Delta was independently isolated and named Delta-1 or Delta-like 1 (Dll1) (Henrique et al., (1995); Chitnis et al., (1995); Bettenhausen, (1995)). Cloning using the polymerase chain reaction has yielded three more Delta homologs and three Serrate homologs (Nye and Kopan, (1995)).

The effects of Notch signaling on molecular and cellular events have been studied using constitutively activated derivatives of Notch, and these studies have demonstrated that the activated intracellular derivatives of Notch have significant inhibitory effects on myogenesis and neurogenesis during Xenopus development and in mammalian cell culture systems that undergo differentiation (Coffman et al., Cell 73:659–661 (1993); Kopan et al., Development 120:2385–2396 (1994); Nye et al., Development 120:2421–2430 (1994)).

The present invention relates to the ability of the fringe A and B proteins encoded by the fringe genes described herein to signal to or activate members of the DSL family of transmembrane proteins, which in turn bind to the Notch receptor and affect the differentiation and development of embryonic tissue. Thus, the fringe genes and proteins described herein are early regulators of tissue differentiation and development, upstream from the DSL/Notch receptor signalling mechanism. The secreted fringe proteins induce members of the DSL protein family, which in turn bind to the Notch receptor to affect lateral cell signalling.

The present invention also pertains to isolated DNA encoding a polypeptide having at least one biological activity of a vertebrate fringe protein, as well as to the polypeptide or protein encoded thereby. In one embodiment, the present invention pertains to DNA encoding the fringe A (radical fringe) and fringe B (lunatic fringe) proteins and comprising the nucleic acid sequences of SEQ ID NOS: 1 and 6, respectively (FIGS. 1A–B and 2A–B, respectively). The present invention also pertains to the fringe A protein comprising the amino acid sequence of SEQ ID NO: 5 (FIGS. 1A–B) and the fringe B protein comprising the amino acid sequence of SEQ ID NO: 7 (FIGS. 2A–B). The present invention also relates to an isolated polypeptide having at least one biological activity of a vertebrate fringe protein and comprising the amino acid sequence of SEQ ID NO: 5 or SEQ ID NO: 7. As defined herein, "isolated" DNA or protein includes isolation from the native environment of the cell or organism, recombinantly produced, or chemically synthesized DNA or proteins.

In another aspect of the invention, the nucleic acid sequence of the DNA encoding a polypeptide having at least one biological activity of a vertebrate fringe protein is at least 30 percent identical with the nucleic acid sequence of either SEQ ID NO: 1 or 6. Another subject of the invention are fringe proteins having an amino acid sequence which is at least 30 percent similar to the carboxy-terminal 60–75% of the amino acid sequence of SEQ ID NOS: 5 or 7, as well as the DNA encoding such proteins. The present invention also relates to polypeptides having at least one biological activity of a vertebrate fringe protein and having an amino acid sequence comprising six conserved cysteine residues located within the conserved carboxy-terminal 60–75% of the amino acid sequence.

As used herein, the term "similar" with respect to amino acids means amino acid residues which are either identical or which represent a conserved change. For example, it is reasonable to expect that an isolated replacement of a leucine with an isoleucine or valine, an aspartate with a glutamate, a threonine with a serine, or a similar replacement of an amino acid with a structurally related amino acid (i.e., conservative replacements) will not have a significant effect on the biological activity of the resulting molecule. Conservative replacements are those that take place within a family of amino acids that are related in their side chains (e.g., acidic, basic, nonpolar, uncharged polar, aliphatic, amide, sulfur-containing and aromatic) (see, for example, *Biochemistry* 2nd ed., ed. L. Stryer (W. H. Freeman and Co., 1981). Whether a change in the amino acid sequence of a polypeptide results in a functional fringe homolog can be readily determined by assessing the ability of the variant polypeptide to produce a response in cells in a manner similar to the wild-type or unchanged fringe. Polypeptides in which more than one replacement has taken place can also be tested in the same manner.

The present invention also pertains to nucleic acid sequences which hybridize to the nucleic acid sequences of either SEQ ID NO: 1 or 6 under hybridization conditions of medium stringency. Stringency conditions which are appropriately termed "medium stringency" are known to those skilled in the art or can be found in standard texts such as *Current Protocols in Molecular Biology*, John Wiley & Sons, New York (1989), 6.3.1–6.3.6.

Exemplary biological activity which the vertebrate proteins or polypeptides of the present invention, including the fringe A protein, may have includes the ability to affect neural-specification of cell type identity, proliferative regulation of migratory paths, proliferation of neural crest (branchial arches), definition of morphological boundaries, including morphological boundaries of the limb, cell shape decisions and indirect regulation of proliferative signals.

Other biological activity which the vertebrate proteins and polypeptides of the present invention, including the fringe B protein, may have includes the ability to affect proliferative and fate specification signals of neural tissues, regulation of formation of components of ear, nose and facial structures, induction, patterning and proliferation of vasculature, and fate specification within somitic tissues.

The present invention also provides expression vectors containing a nucleic acid sequence encoding a fringe polypeptide or a polypeptide having at least one activity of a fringe polypeptide, operably linked to at least one regulatory sequence. Operably linked is intended to mean that the nucleotide sequence is linked to a regulatory sequence in a manner which allows expression of the nucleic acid sequence. Regulatory sequences are art-recognized and are selected to direct expression of the nucleic acid sequence to produce a polypeptide having at least one activity of a fringe protein. Accordingly, the term regulatory sequence includes promoters, enhancers and other expression control elements. Such regulatory sequences are described in Goeddel, *Gene Expression Technology: Methods in Enzymology* 185, Academic Press, San Diego, Calif. (1990)). It should be understood that the design of the expression vector may depend on such factors as the choice of the host cell to be transformed and/or the type of protein desired to be expressed.

Prokaryotic and eukaryotic host cells transfected by the described vectors are also a subject of this invention. For instance, cells which can be transfected with the vectors of the present invention include, but are not limited to, bacterial cells such as *E. coli*, insect cells (baculovirus), yeast, or mammalian cells such as Chinese hamster ovary cells (CHO).

Thus, a nucleotide sequence derived from the cloning of the vertebrate fringe polypeptides or proteins of the present invention, encoding all or a selected portion of the protein, can be used to produce a recombinant form of fringe via microbial or eukaryotic cellular processes. Ligating the polynucleotide sequence into a gene construct, such as an expression vector, and transforming or transfecting into hosts, either eukaryotice (yeast, avian, insect or mammalian) or prokaryotic (bacterial cells), are standard procedures used in producing other well-known proteins, e.g., insulin, interferons, human growth hormone, IL-1, IL-2 and similar proteins. Similar procedures, or modifications thereof, can be employed to prepare recombinant fringe proteins or polypeptides, by microbial means or tissue-culture technology in accord with the subject invention. Depending on the expression system chosen, the ability to obtain a recombinant protein which is either glycosylated or not can be controlled.

The recombinant fringe protein can be produced by ligating the cloned gene, or a portion thereof, into a vector suitable for expression in either prokaryotic cells, eukaryotic cells or both (see, for example, Broach et al., *Experimental Manipulation of Gene Expression*, ed. M. Inouye (Academic Press, 1983) p. 83; *Molecular Cloning: A Laboratory Manual*, 2nd Ed., ed. Sambrook et al., (Cold Spring Harbor Laboratory Press, 1989) Chapters 16 and 17). Expression vehicles for production of recombinant fringe include plasmids and other vectors. For instance, suitable vectors for the expression of fringe include but are not limited to plasmids of the types: pBR322-derived plasmids, pEMBL-derived plasmids, pEX-derived plasmids, pBTac-derived plasmids, and pUC-derived plasmids for expression in prokaryotic cells, such as *E. coli*.

The present invention further pertains to methods of producing polypeptides which have at least one biological activity of a fringe protein. For example, a host cell transfected with a nucleic acid vector directing expression of a nucleotide sequence encoding a polypeptide having an activity of a vertebrate fringe protein can be cultured under appropriate conditions to allow expression of the polypeptide to occur. The polypeptide may be secreted and isolated from a mixture of cells and medium containing the polypeptide having at least one biological activity of a vertebrate fringe protein. Alternatively, the polypeptide can be retained cytoplasmically and the cells harvested, lysed and the polypeptide isolated. The polypeptide can be isolated from cell culture medium, host cells, or both using techniques known in the art for purifying proteins including ion-exchange chromatography, gel filtration chromatography, ultrafiltration, electrophoresis and immunoaffinity purification with antibodies specific for a polypeptide having at least one biological activity of a vertebrate fringe protein.

In another embodiment, fusion proteins can also facilitate the expression of proteins, such as the fringe proteins of the present invention. For example, the fringe protein can be generated as a glutathione-S-transferase (GST) fusion protein. Such GST fusion proteins can enable easy purification of the fringe protein, such as by the use of glutathione-derived matrices (see, for example, *Current Protocols in Molecular Biology*, eds: Ausabel et al. (New York: John Wiley & Sons (1991)).

The present invention also provides compositions which are suitable for pharmaceutical administration. The fringe proteins of the present invention, or polypeptides having at least one biological activity of a fringe protein, can be formulated with a physiologically acceptable medium to prepare a pharmaceutical composition. The particular physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to procedures well known to medicinal chemists, and will depend on the ultimate pharmaceutical formulation desired. Methods of introduction of exogenous fringe at the site of treatment include, but are not limited to, intradermal, intramuscular, intraperitoneal, intravenous, subcutaneous, oral and intranasal. Other suitable methods of introduction can also include rechargeable or biodegradable devices and slow release polymeric devices. The pharmaceutical fringe composition can also be administered as part of a combinatorial therapy with other agents.

Another aspect of the invention pertains to an antibody specifically reactive with a polypeptide having at least one biological activity of a vertebrate fringe protein. For example, by using peptides having an activity of a vertebrate fringe protein, anti-protein/anti-peptide antisera or monoclonal antibodies can be made using standard methods. A mammal such as a mouse, a hamster or rabbit can be immunized with an immunogenic form of the polypeptide (i.d., an antigenic fragment of the polypeptide which is capable of eliciting an antibody response). Techniques for conferring immunogenicity on a protein or peptide include conjugation to carriers or other techniques will known in the art. A peptide having at least one biological activity of a fringe protein can be administered in the presence of an adjuvant. The progress of immunization can be monitored by detection of antibody titers in plasma or serum. Standard ELISA or other immunoassays can be used with the immunogen as antigen to assess the levels of antibodies.

Following immunization, anti-fringe antisera can be obtained, and if desired, polyclonal anti-fringe antibodies can be isolated from the serum. Monoclonal antibodies can also be produced by standard techniques which are well known in the art, such as the hybridoma technique (Kohler and Milstein *Nature* 256:495–497 (1975)), the human B cell hybridoma technique (Kozbar et al., *Immunology Today* 4:72 (1983)) and the EBV-hybridoma technique (Cole et al., *Monoclonal Antibodies and Cancer Therapy*, Alan R. Liss, Inc., pp. 77–96 (1985)).

In addition, nucleotide probes can be generated from the cloned sequences of the fringe proteins which allow for histological screening of intact tissue and tissue samples for the presence of fringe mRNA. These probes can be used for both predictive and therapeutic evaluation of allelic mutations which might be manifest in, for example, birth defects. Used in conjunction with anti-fringe antibody immunoassays, the nucleotide probes can help facilitate the determination of the molecular basis for a developmental disorder which may involve some abnormality associated with expression (or decrease in or lack thereof) of a fringe polypeptide or protein.

The present invention also features non-human transgenic embryos which ectopically express a fringe gene taken from another species (see, for example, U.S. Pat. No. 4,873,316 (Meade et al.) and U.S. Pat. No. 5,215,904 (Goulde et al.)). For example, a mouse embryo can be transfected with a DNA construct containing a chicken fringe gene. Such transgenic manipulations are useful to study the conservation in function of various fringe homologs across species.

The present invention will also facilitate further determination of the potential role of the fringe proteins in cell fate and development. In vitro cell cultures can be used for the identification, isolation, and study of genes and gene products that are expressed in response to the presence of fringe; these genes would be downstream of the fringe signal. For example, if new transcription is initiated by the fringe signal, a subtractive cDNA library (Wang et al. *PNAS USA* 88:11505–11509 (1991)) prepared with control cells and cells treated with fringe can be used to isolate genes that are turned on or off by the fringe signal. Once isolated, the genes regulated by fringe induction can be sequenced and their embryonic distribution can be determined by in situ hybridization approaches. If their embryonic expression is in agreement with the particular differentiation pattern being studied, they can be tested for that differentiating activity in cell culture and in embryos or organisms.

The following criteria can be used, alone or in combination, to determine whether a particular gene, which is associated with development or differentiation, is regulated by the fringe gene or genes: (1) the RNA of the putatively regulated gene appears quickly following application of fringe; (2) the induction of the putatively regulated gene does not require previous protein synthesis; (3) where fringe is provided as a soluble factor, immediate early response genes should be expressed as a result of contact with fringe and not from a secondary cell-cell interaction; and (4) the putatively regulated gene should be present and activated in the appropriate tissue during the particular differentiation being studied.

A further use of the invention concerns the therapeutic application of a fringe protein, or an agonist or antagonist thereof, to enhance survival of or increase the differentiation of particular tissues or cells in various systems throughout the body. The ability of fringe to regulate differentiation during development and also presumably in the adult state indicates that fringe can be reasonably expected to facilitate control of adult cells with regard to maintenance, functional performance and aging of normal cells; repair and regeneration processes in chemically or mechanically lesioned cells; and prevention of degeneration and premature death which result from a loss of differentiation in certain pathological conditions. In light of this knowledge, the present invention can be used in the treatment of, prevention and/or reduction of the severity of various disorders, including disorders of the vasculature system such as varicosities and atherosclerosis. Particularly since the subject fringe proteins appear to be involved in committing cells to form blood vessels, the fringe proteins of the present invention can also be used in the treatment of tumor pathogenesis, i.e., the ability to block the activity of the fringe proteins can be useful in preventing the establishment or maintenance of the blood supply to solid tumors. The fringe proteins of the present invention are also useful in wound healing, in that the augmentation of fringe activity, and thus the augmentation of angiogenesis, may aid in speeding the recovery of wounded regions of the body.

The present invention, by making available purified or isolated fringe proteins, allows the development of assays which can be used to identify drugs or agents with are either agonists or antagonists of fringe activity. By mutagenesis, and other structural surveys of the fringe protein family, rational drug design can be employed to manipulate fringe A or B or portions thereof, as either agonists or antagonists, as well as to facilitate design of small molecule agonists and antagonists.

The present invention also provides assays for identifying agents which alter the expression of a fringe gene or which alter the differentiation or development of an organism which is associated with the expression of a fringe gene. For example, the assay can be used to identify agents which alter the formation of angiogenic precursors or angiogenic cells or the AER or which alter the formation or subdivision of the neural tube. In the context of the present invention, the term "alters" includes both increasing and decreasing the differentiation of the organism, as well as changing the differentiation pattern of the organism.

For example, an organism can be treated with the agent to be tested, and the expression pattern of the fringe A and/or fringe B genes can be assessed and compared with their respective expression patterns in a control organism in the absence of the agent to be tested. An increase in the expression of a particular fringe gene indicates that the agent is an agonist of at least one biological activity of, or has a positive effect on the expression of, that fringe gene. Similarly, a decrease in the expression of the fringe gene indicates that the agent is an antagonist of at least one biological activity of, or has a negative effect on, that fringe gene.

Alternatively, a similar assay is provided for identifying an agent which alters the formation of angiogenic precursors or angiogenic cells. For example, an agent to be tested can be administered to an organism, and the expression of fringe B in the test organism can be assessed in tissue or cells in which angiogenic precursors are formed, and the expression can be compared with the expression of fringe B in a control organism in the absence of the agent to be tested. A difference in the expression of fringe B indicates that the agent alters the formation of angiogenic precursors or angiogenic cells. The same assay can be used to identify agents which alter the formation of the apical ectodermal ridge (AER) by assessing the expression of fringe A in place of fringe B. The same assay can be used to identify agents which alter the formation or subdivision of the neural tube by assessing the expression of fringe A and/or fringe B.

As defined herein, "expression" of the fringe genes includes both the location and extent or quantitative amount of expression in the organism. Furthermore, the comparison between the test organism and the control organism can be in terms of the whole organism (i.e., the expression as a whole) or in terms of comparable portions or tissues of the organisms.

As described in the following examples, the DNA clones provided by the present invention were obtained by first screening a chick cDNA library with a partial human fringe cDNA clone. Positive plaques were identified and two chicken clones were selected. These clones were then used as probes to obtain genomic clones containing the coding sequence of the chicken fringe A and B genes.

In order to identify other chicken fringe homologs, the chicken fringe A and B clones were used to probe a genomic Southern blot containing chicken DNA. These results indicate that there is an additional chicken fringe gene (fringe C). This methodology can also be used to identify other vertebrate fringe homologs.

As described in the Examples, Northern blots and in situ hybridization demonstrated that the chicken fringe A gene is expressed early (from approximately HH stage 12 on (Hamburger & Hamilton, *J. Exp. Morph.* 88:49–92 (1951))) in anterior neural tube/brain, surface ectoderm, ectodermal borders between branchial arches, otocyst, dermomyotomal compartment of somites, and dorsal limb ectoderm, with most concentration at the dorsal/ventral boundary just prior to apical ectodermal ridge (AER) formation, then restricted to the AER through at least stage 25.

Northern blots and in situ hybridization also demonstrated that the chicken fringe B gene is expressed in the early (stage 6+, just post-gastrulation) stripe in presomitic mesoderm, which may indicate presumptive somite, and also in the dorsal neural fold. Neural tube expression evolves into a series of six stripes running longitudinally the length of the CNS from tail to rostral forebrain, at least through day 10 of development. Expression of fringe B is restricted primarily to proliferative layers and is excluded from absolute dorsal and ventral regions. Fringe B is also expressed in a single stripe within the otocyst, within the complete nasal placode, within a subset of migrating branchial neural crest. Somitic expression evolves to the dermomyotome, which then devolves to a dorsal and ventral component. The ventral expression is restricted to the lateral epithelium which gives rise to epaxial muscle and dermis. The dorsal component may be blood vessel precursors, as later (day 4 and on) expression is seen in a meshwork of smaller blood vessels throughout the body.

From the expression pattern results detailed in the Examples and described above, it appears that fringe A functions in the neural specification of cell type identity, proliferative regulation of migratory pathways, neural crest/branchial arch proliferation, definition of morphological boundaries, cell shape, limb specification of morphological boundaries and indirect regulation of proliferative signals. As described herein, fringe A has been shown to be an early marker for development of the AER, as it is expressed both in the formed AER and in cells which are AER precursors, i.e., destined to form the AER. Further, it appears that fringe B functions in proliferative and fate specification signals of neural tissues, regulation of the development of components of the ear, nose and facial structure, induction, patterning and proliferation of vasculature, and fate specification within somitic tissues.

It has been shown that the pattern of fringe B gene expression is similar to the expression pattern of the Delta homolog Delta-1 (Dll1) in the primary neurons of the central nervous system and posterior mesoderm of the developing chicken embryo. This similarity of expression may indicate that fringe B has a direct role in the regulation of the Delta-1/Notch signalling pathway.

It has also been shown that the pattern of fringe A expression is complementary to the pattern of expression of the Serrate homolog Serrate-1, producing a striped expression pattern. This complementary expression pattern may indicate that fringe A is an indirect regulator of Serrate-1. However, the expression pattern of fringe A has been shown to be similar to the expression pattern of Serrate homolog Serrate-2 in the AER of the developing chicken embryo, perhaps indicating a direct regulation, as in the fringe B/Delta-1 relationship.

Fringe proteins, including the chicken fringe A and B proteins described herein and the Drosophila fringe protein described in Irvine & Wieschaus, *Cell* 79:595–606 (1994), appear to be divided into 3 portions. The first portion, comprising 30–35 amino acids, appears to define a signal peptide in each protein. The second portion, which extends in fringe A through amino acid 104, in fringe B through amino acid 97 and in Drosophila fringe through amino acid 147, shows little or no conservation of sequence. The third portion, herein called the "conserved region", comprises the carboxy-terminal 60–75% of the protein, and this portion of each protein comprises six conserved cysteines at equivalent positions (FIGS. 4A–B). In fringe A, these positions are amino acid residues 160, 171, 189, 253, 357 and 366 (FIGS. 1A–B); in fringe B, these positions are amino acid residues 152, 163, 181, 244, 348 and 359 (FIGS. 2A–B). This conserved region, and in particular the conserved cysteines, appear to be important to the function of the fringe protein, and the presence or absence of the conserved region and/or the conserved cysteine residues is a particularly helpful characteristic which can be used to identify other members of the vertebrate or invertebrate fringe protein family.

Accordingly, this invention also relates to polypeptides or proteins which have greater than about 30% identity to the amino acid sequence of the conserved region of fringe A or fringe B. This invention also pertains to polypeptides or proteins which have conserved cysteine residues at positions equivalent to the positions of the conserved cysteine residues in the conserved region (FIGS. 4A–B).

Terms used herein are intended to have their art-recognized meaning unless otherwise defined. Teachings of the references cited herein are hereby incorporated herein by reference.

The following examples are offered for the purpose of illustrating the present invention and are not to be construed to limit the scope of the present invention:

EXAMPLES
Cloning of Vertebrate fringe Genes 600,000 plaques of a HH stage 12–15 whole chick embryo library cloned in the lambda ZAP vector were screened with the inserts of expressed sequence tags c-32h10 (Genbank F11888) and c-3md09 (Genbank F13368). The filters were hybridized at 30° C. in 50% deionized formamide, 2×SSC, 10% dextran sulfate, 1% SDS and washed at 50° C. in 2×SSC, 1% SDS. Plaques containing partial cDNA clones of both fringe A and fringe B were isolated, and their inserts used to rescreen the library under the same conditions. Full length cDNAs were isolated in the rescreen, and their sequences determined by the dideoxy chain termination method (Sanger et al., *PNAS USA* 74:5463–5467 (1977)) using Sequenase v2.0 T7 DNA polymerase (U.S. Biochemicals).

Whole-Mount In Situ Hybridization

Whole-mount in situ hybridization was performed using procedures modified from Parr et al. (*Development* 119:247–261 (1993)), Sasaki and Hogan (*Development* 118:47–59 (1993)) and Rosen and Beddington (*Trends Genet.* 9:162–167 (1993). Chick embryos were removed from the egg, and extraembryonic membranes were dissected in calcium-free and magnesium-free phosphate-buffered saline (PBS) at room temperature. Unless otherwise noted, all washes are for 5 minutes at room temperature. Embryos were fixed overnight at 4° C. with 4% paraformaldehyde in PBS, washed twice with PBT (PBS with 0.1% Tween 20) at 4° C., and dehydrated through an ascending methanol series in PBT (25%, 50%, 75%, 2×100% methanol). Embryos were stored at −20° C. until further use.

Both prelimb bud and limb bud stage embryos were rehydrated through a descending methanol series followed by two washes in PBT. Limb bud stage embryos were bleached in 6% hydrogen peroxide in PBT, washed three times with PBT, permeabilized with proteinase K (Boehringer Mannheim, 2 μg/ml) for 15 minutes, washed with 2 mg/ml glycine in PBT for 10 minutes and washed twice with PBT. Prelimb bud stage embryos were permeabilized (without prior incubation with hydrogen peroxide) by three 30 minute washes in RIPA buffer (150 mM NaCl, 1% Nonidet p-40, 0.5% deoxycholate, 0.1% SDS, 1 mM EDTA, 50 mM Tris-HCl [pH 8.0]). In all subsequent steps, prelimb bud and limb bud stage embryos were treated equivalently. Embryos were fixed with 4% paraformaldehyde plus 0.2% gluteraldehyde in PBT, washed four times with PBT, washed once with prehybridization buffer (50% formamide, 5×SSC, 1% SDS, 50 μg/ml total yeast RNA, 50 μg/ml heparin [pH 4.5]), and incubated with fresh prehybridization buffer for 1 hour at 70° C. The prehybridization buffer was then replaced with hybridization buffer (prehybridization buffer with digoxigenin-labeled riboprobe at 1 μg/ml) and incubated overnight at 70° C.

Following hybridization, embryos were washed three times for 3 minutes each time at 70° C. with solution 1 (50% formamide, 5×SSC, 1% SDS [pH 4.5]), three times for 30 minutes each time at 70° C. with solution 3 (50% formamide, 2×SSC [pH 4.5]), and three times at room temperature with tris-buffered saline (TBS, with 2 mM levamisole) containing 1% Tween 20. Nonspecific binding of antibody was prevented by preblocking embryos in TBS plus 1% Tween 20 containing 10% heat-inactivated sheep serum for 2.5 hours at room temperature and by preincubating anti-digoxigenin Fab alkaline phosphatase conjugate (Boehringer Mannheim) in TBS plus 1% Tween 20 containing heat-inactivated 1% sheep serum and approximately 0.3% heat-inactivated chick embryo powder. After an overnight incubation at 4° C. with the preadsorbed antibody in TBS plus 1% Tween 20 containing 1% sheep serum, embryos were washed three times for 5 minutes each time at room temperature with TBS plus 1% Tween 20, five times for 1.5 hours each time at room temperature with TBS plus 1% Tween 20, and overnight with TBS plus 1% Tween 20 at 40° C. The buffer was exchanged by washing three times for 10 minutes each time with NTMT (100 mM NaCl, 100 mM Tris-HCl, 50 mM $MgCl_2$, 1% Tween 20, 2 mM levamisole). The antibody detection reaction was performed by incubating embryos with detection solution (NTMT with 0.25 mg/ml nitroblue tetrazolium and 0.13 mg/ml 5-bromo-4-chloro-3-indolyl-phosphate toluidinium). In general, prelimb bud stage embryos were incubated for 5–15 hours and limb bud stage embryos for 1–5 hours. After the detection reaction was deemed complete, embryos were washed twice with NTMT, once with PBT (pH 5.5), postfixed with 4% paraformaldehyde/0.1% glutaraldehyde in PBT, and washed several times with PBT. In some cases, embryos were cleared through a series of 30%, 50%, 70% and 80% glycerol in PBT. Whole embryos were photographed under transmitted light using a Nikon zoom stereo microscope with Kodak Ektar 100 ASA film. Selected embryos were processed for frozen sections by dehydration in 30% sucrose in PBS followed by embedding in gelatin and freezing. Cryostat sections (25 μm) were collected on superfrost plus slides (Fisher), rehydrated in PBS, and mounted with gel-vatol. Sections were photographed with Nomarski optics using a Zeiss Axiophot microscope and Kodak Ektar 25 ASA film.

Equivalents

Those skilled in the art will recognize or be able to ascertain, using no more than routine experimentation, many equivalents to the specific embodiments of the invention described herein. Such equivalents are intended to be encompassed in the scope of the following claims.

We claim:

1. Isolated DNA encoding a vertebrate fringe polypeptide comprising a nucleic acid sequence selected from the group consisting of:
   a) SEQ ID NO: 1;
   b) SEQ ID NO: 6; and
   c) SEQ ID NO: 8.

2. An expression vector comprising DNA according to claim 1 operably linked to at least one regulatory sequence.

3. A isolated host cell comprising an expression vector according to claim 2.

4. A method for producing a vertebrate fringe polypeptide comprising culturing a host cell according to claim 3 under conditions suitable for production of the encoded polypeptide and recovering said fringe polypeptide.

* * * * *

UNITED STATES PATENT AND TRADEMARK OFFICE
CERTIFICATE OF CORRECTION

PATENT NO. : 6,054,298
DATED : April 25, 2000
INVENTOR(S) : Edward M. Laufer, Olivia E. Orozco and Clifford J. Tabin It is certified that error appears in the above-indentified patent and that said Letters Patent is hereby corrected as shown below:

In Column 37, last line: After the words "at least one" and before the word "regulatory", insert --transcriptional--.

Signed and Sealed this

Twenty-seventh Day of February, 2001

Attest:

NICHOLAS P. GODICI

Attesting Officer

Acting Director of the United States Patent and Trademark Office

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 1120 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: join(1..240, 244..474, 478..531, 538..579, 583
          ..678, 682..687, 691..807, 811..843, 850..870,
          874..990, 994..1056, 1060..1083, 1087..1104, 1108
          ..1119)

(xi) SEQUENCE DESCRIPTION: SEQ ID NO:1:

```
ATG AGC AGC TCC TGC CTG GGG CTC CGC AGA GCC TGC TTC CTG CTG TCC        48
Met Ser Ser Ser Cys Leu Gly Leu Arg Arg Ala Cys Phe Leu Leu Ser
 1               5                  10                  15

GTC ACC GCC GCC GCC GTT CTC CTG CTG CTG CTC GCC CCG GGG ACA GCC        96
Val Thr Ala Ala Ala Val Leu Leu Leu Leu Leu Ala Pro Gly Thr Ala
             20                  25                  30

CCC CGC CGC GCC CCG CCG CCG CCC GCC GCC CGC CGG GCC CAG CAG GCC       144
Pro Arg Arg Ala Pro Pro Pro Pro Ala Ala Arg Arg Ala Gln Gln Ala
         35                  40                  45

CTC CCC GAA GCG GGA GGC GCG GCC CGC GGG GAG CGA CGT GCC CGG GGA       192
Leu Pro Glu Ala Gly Gly Ala Ala Arg Gly Glu Arg Arg Ala Arg Gly
     50                  55                  60

CCG CGG CGG CGG CTC GGG AGC CGC GGG GGG CGG CCG GGG CGT CGC CGG       240
Pro Arg Arg Arg Leu Gly Ser Arg Gly Gly Arg Pro Gly Arg Arg Arg
 65                  70                  75                  80

TAG CCC GTG GCC TTC GCG GAG GGT CCG CAT GGG GCC TCC CGG CGG CTC       288
    Pro Val Ala Phe Ala Glu Gly Pro His Gly Ala Ser Arg Arg Leu
                     85                  90                  95

GGC CAA GGA GAG CCT GGA GCT AAA AGA CAT CTT TAT TGC GGT GAA AAC       336
Gly Gln Gly Glu Pro Gly Ala Lys Arg His Leu Tyr Cys Gly Glu Asn
                100                 105                 110

GAC GAG GAA GTA TCA CAA GAC GCG GCT GGA GCT GCT GTT CCA AAC CTG       384
Asp Glu Glu Val Ser Gln Asp Ala Ala Gly Ala Ala Val Pro Asn Leu
            115                 120                 125

GAT CTC CCG GGC GAG AGG ACA GAC ATT CAT ATT CAC AGA CTG GGA GGA       432
Asp Leu Pro Gly Glu Arg Thr Asp Ile His Ile His Arg Leu Gly Gly
        130                 135                 140

TCG AGA GCT GCG CCT GAA AGC AGG GGA TCA TAT GAT CAA CAC                474
Ser Arg Ala Ala Pro Glu Ser Arg Gly Ser Tyr Asp Gln His
145                 150                 155

TAA CTG TTC TGC TGT CCA CAC CCG GCA AGC TCT GTG CTG CAA GAT GTC       522
    Leu Phe Cys Cys Pro His Pro Ala Ser Ser Val Leu Gln Asp Val
                160                 165                 170

TGT GGA ATA TGATAA ATT CCT AGA ATC TGG ACA AAA GTG GTT TTG CCA        570
Cys Gly Ile        Ile Pro Arg Ile Trp Thr Lys Val Val Leu Pro
        175                     180                 185

TGT GGA CGA TGA CAA CTA TGT GAA TCC ACG GAC TCT CTT GCG TCT CTT       618
Cys Gly Arg     Gln Leu Cys Glu Ser Thr Asp Ser Leu Ala Ser Leu
        190                 195                 200
```

```
ATC TGC CTT CTC ACC CAG CCA GGA TGT CTA TGT GGG ACG ACC GAG TCT      666
Ile Cys Leu Leu Thr Gln Pro Gly Cys Leu Cys Gly Thr Thr Glu Ser
            205                 210                 215

GGA CCA TCC CAT TGA AGC AGC TGA CCA TGT CCA AAG CGA TGG ATC AAA      714
Gly Pro Ser His     Ser Ser     Pro Cys Pro Lys Arg Trp Ile Lys
            220                     225                 230

GAC AAG CGT GAA ATT CTG GTT TGC CAC AGG TGG AGC AGG GTT CTG TAT      762
Asp Lys Arg Glu Ile Leu Val Cys His Arg Trp Ser Arg Val Leu Tyr
            235                 240                 245

CAG CAG AGG TCT TGC TCT GAA GAT GAG TCC CTG GGC CAG CCT GGG          807
Gln Gln Arg Ser Cys Ser Glu Asp Glu Ser Leu Gly Gln Pro Gly
            250                 255                 260

TAA TTT CAT CAG TAC TGC AGA AAG AGT GCG TCT TCC TGATGA CTG CAC       855
    Phe His Gln Tyr Cys Arg Lys Ser Ala Ser Ser         Leu His
            265                 270                             275

CAT TGG CTA CAT CAT TGA AGG GCT GCT GGA AGT AAA GCT GCT GCA CAG      903
His Trp Leu His His     Arg Ala Ala Gly Ser Lys Ala Ala Ala Gln
            280                     285                 290

CCC ATT GTT CCA TTC CCA TCT GGA AAA TCT GCA GAG ACT ACA AGG AGA      951
Pro Ile Val Pro Phe Pro Ser Gly Lys Ser Ala Glu Thr Thr Arg Arg
            295                 300                 305

GTC TGT GCT GCA ACA GGT AAC CCT AAG TTA TGG GGA CCC TGA GAA CAA      999
Val Cys Ala Ala Thr Gly Asn Pro Lys Leu Trp Gly Pro     Glu Gln
            310                 315                     320

ACA CAA TGT TGT GAG TGT GGG AGG AGT GTT TGG ACT TCA GCA AGA CCC     1047
Thr Gln Cys Cys Glu Cys Gly Arg Ser Val Trp Thr Ser Ala Arg Pro
            325                 330                 335

AAC CAG ATT TAA ATC TGT CCA TTG TCT TCT TTA CCC TGA CAC TAT TTG     1095
Asn Gln Ile     Ile Cys Pro Leu Ser Ser Leu Pro     His Tyr Leu
            340                 345                     350

GTG CCC CAA TAA GAA GAT GTC ATA A                                   1120
Val Pro Gln     Glu Asp Val Ile
            355
```

(2) INFORMATION FOR SEQ ID NO:2:

(i) SEQUENCE CHARACTERISTICS:
        (A) LENGTH: 358 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Ser Cys Leu Gly Leu Arg Arg Ala Cys Phe Leu Leu Ser
 1               5                  10                  15

Val Thr Ala Ala Val Leu Leu Leu Leu Ala Pro Gly Thr Ala
                20                  25                  30

Pro Arg Arg Ala Pro Pro Pro Ala Ala Arg Arg Ala Gln Gln Ala
                35                  40                  45

Leu Pro Glu Ala Gly Gly Ala Arg Gly Glu Arg Ala Arg Gly
        50                  55                  60

Pro Arg Arg Arg Leu Gly Ser Arg Gly Gly Arg Pro Gly Arg Arg
 65                 70                  75                  80

Pro Val Ala Phe Ala Glu Gly Pro His Gly Ala Ser Arg Arg Leu Gly
                85                  90                  95

Gln Gly Glu Pro Gly Ala Lys Arg His Leu Tyr Cys Gly Glu Asn Asp
                100                 105                 110
```

-continued

```
Glu Glu Val Ser Gln Asp Ala Ala Gly Ala Ala Val Pro Asn Leu Asp
        115                 120                 125

Leu Pro Gly Glu Arg Thr Asp Ile His Ile His Arg Leu Gly Gly Ser
130                 135                 140

Arg Ala Ala Pro Glu Ser Arg Gly Ser Tyr Asp Gln His Leu Phe Cys
145                 150                 155                 160

Cys Pro His Pro Ala Ser Ser Val Leu Gln Asp Val Cys Gly Ile Ile
                165                 170                 175

Pro Arg Ile Trp Thr Lys Val Val Leu Pro Cys Gly Arg Gln Leu Cys
            180                 185                 190

Glu Ser Thr Asp Ser Leu Ala Ser Leu Ile Cys Leu Leu Thr Gln Pro
        195                 200                 205

Gly Cys Leu Cys Gly Thr Thr Glu Ser Gly Pro Ser His Ser Ser Pro
210                 215                 220

Cys Pro Lys Arg Trp Ile Lys Asp Lys Arg Glu Ile Leu Val Cys His
225                 230                 235                 240

Arg Trp Ser Arg Val Leu Tyr Gln Gln Arg Ser Cys Ser Glu Asp Glu
                245                 250                 255

Ser Leu Gly Gln Pro Gly Phe His Gln Tyr Cys Arg Lys Ser Ala Ser
            260                 265                 270

Ser Leu His His Trp Leu His His Arg Ala Ala Gly Ser Lys Ala Ala
        275                 280                 285

Ala Gln Pro Ile Val Pro Phe Pro Ser Gly Lys Ser Ala Glu Thr Thr
        290                 295                 300

Arg Arg Val Cys Ala Ala Thr Gly Asn Pro Lys Leu Trp Gly Pro Glu
305                 310                 315                 320

Gln Thr Gln Cys Cys Glu Cys Gly Arg Ser Val Trp Thr Ser Ala Arg
                325                 330                 335

Pro Asn Gln Ile Ile Cys Pro Leu Ser Ser Leu Pro His Tyr Leu Val
            340                 345                 350

Pro Gln Glu Asp Val Ile
        355
```

(2) INFORMATION FOR SEQ ID NO:3:

(i) SEQUENCE CHARACTERISTICS:
        (A) LENGTH: 371 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Ala Ala Pro Ala Trp Gly Ser Ala Glu Pro Ala Ser Cys Cys Pro Ser
1               5                   10                  15

Pro Pro Pro Pro Phe Ser Cys Cys Ser Pro Arg Gly Gln Pro Pro
                20                  25                  30

Ala Ala Pro Arg Arg Pro Pro Ala Gly Pro Ser Arg Pro Ser
            35                  40                  45

Pro Lys Arg Glu Ala Arg Pro Ala Gly Ser Asp Val Pro Gly Asp Arg
        50                  55                  60

Gly Gly Gly Ser Gly Ala Ala Gly Gly Arg Gly Val Ala Gly Ser
65                  70                  75                  80

Pro Trp Pro Ser Arg Arg Val Arg Met Gly Pro Pro Gly Gly Ser Ala
```

-continued

```
                 85                  90                  95
Lys Glu Ser Leu Glu Leu Lys Asp Ile Phe Ile Ala Val Lys Thr Thr
            100                 105                 110

Arg Lys Tyr His Lys Thr Arg Leu Glu Leu Leu Phe Gln Thr Trp Ile
            115                 120                 125

Ser Arg Ala Arg Gly Gln Thr Phe Ile Phe Thr Asp Trp Glu Asp Arg
            130                 135                 140

Glu Leu Arg Leu Lys Ala Gly Asp His Met Ile Asn Thr Asn Cys Ser
145                 150                 155                 160

Ala Val His Thr Arg Gln Ala Leu Cys Cys Lys Met Ser Val Glu Tyr
                165                 170                 175

Asp Lys Phe Leu Glu Ser Gly Gln Lys Trp Phe Cys His Val Asp Asp
                180                 185                 190

Asp Asn Tyr Val Asn Pro Arg Thr Leu Leu Arg Leu Leu Ser Ala Phe
                195                 200                 205

Ser Pro Ser Gln Asp Val Tyr Val Gly Arg Pro Ser Leu Asp His Pro
                210                 215                 220

Ile Glu Ala Ala Asp His Val Gln Ser Asp Gly Ser Lys Thr Ser Val
225                 230                 235                 240

Lys Phe Trp Phe Ala Thr Gly Ala Gly Phe Cys Ile Ser Arg Gly
                245                 250                 255

Leu Ala Leu Lys Met Ser Pro Trp Ala Ser Leu Gly Asn Phe Ile Ser
                260                 265                 270

Thr Ala Glu Arg Val Arg Leu Pro Asp Asp Cys Thr Ile Gly Tyr Ile
                275                 280                 285

Ile Glu Gly Leu Leu Glu Val Lys Leu Leu His Ser Pro Leu Phe His
                290                 295                 300

Ser His Leu Glu Asn Leu Gln Arg Leu Gln Gly Glu Ser Val Leu Gln
305                 310                 315                 320

Gln Val Thr Leu Ser Tyr Gly Asp Pro Glu Asn Lys His Asn Val Val
                325                 330                 335

Ser Val Gly Gly Val Phe Gly Leu Gln Gln Asp Pro Thr Arg Phe Lys
                340                 345                 350

Ser Val His Cys Leu Leu Tyr Pro Asp Thr Ile Trp Cys Pro Asn Lys
                355                 360                 365

Lys Met Ser
370
```

(2) INFORMATION FOR SEQ ID NO:4:

(i) SEQUENCE CHARACTERISTICS:
        (A) LENGTH: 359 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: CDS
        (B) LOCATION: 1..1118

(xi) SEQUENCE DESCRIPTION: SEQ ID NO:4:

```
Glu Gln Leu Leu Pro Gly Ala Pro Gln Ser Leu Leu Pro Ala Val Arg
1               5                   10                  15

His Arg Arg Arg Arg Ser Pro Ala Ala Ala Arg Pro Gly Asp Ser Pro
```

```
                    20                  25                  30
    Pro Pro Arg Pro Ala Ala Ala Arg Pro Pro Gly Pro Ala Gly Pro
                35                  40                  45
    Pro Arg Ser Gly Arg Arg Gly Pro Arg Gly Ala Thr Cys Pro Gly Thr
     50                  55                  60
    Ala Ala Ala Ala Arg Glu Pro Arg Gly Ala Gly Ala Ser Pro Val
     65                  70                  75                  80
    Ala Arg Gly Leu Arg Gly Gly Ser Ala Trp Gly Leu Pro Ala Ala Arg
                    85                  90                  95
    Pro Arg Arg Ala Trp Ser Lys Thr Ser Leu Leu Arg Lys Arg Arg Gly
                100                 105                 110
    Ser Ile Thr Arg Arg Gly Trp Ser Cys Cys Ser Lys Pro Gly Ser Pro
                115                 120                 125
    Gly Arg Glu Asp Arg His Ser Tyr Ser Gln Thr Gly Arg Ile Glu Ser
                130                 135                 140
    Cys Ala Lys Gln Gly Ile Ile Ser Thr Leu Thr Val Leu Leu Ser Thr
    145                 150                 155                 160
    Pro Gly Lys Leu Cys Ala Ala Arg Cys Leu Trp Asn Met Ile Asn Ser
                    165                 170                 175
    Asn Leu Asp Lys Ser Gly Phe Ala Met Trp Thr Met Thr Thr Met Ile
                    180                 185                 190
    His Gly Leu Ser Cys Val Ser Tyr Leu Pro Ser His Pro Ala Arg Met
                    195                 200                 205
    Ser Met Trp Asp Asp Arg Val Trp Thr Ile Pro Leu Lys Gln Leu Thr
        210                 215                 220
    Met Ser Lys Ala Met Asp Gln Arg Gln Ala Asn Ser Gly Leu Pro Gln
    225                 230                 235                 240
    Val Glu Gln Gly Ser Val Ser Ala Glu Val Leu Leu Arg Val Pro Gly
                    245                 250                 255
    Pro Ala Trp Val Ile Ser Ser Val Leu Gln Lys Glu Cys Val Phe Leu
                    260                 265                 270
    Met Thr Ala Pro Leu Ala Thr Ser Leu Lys Gly Cys Trp Lys Ser Cys
                    275                 280                 285
    Cys Thr Ala His Cys Ser Ile Pro Ile Trp Lys Ile Cys Arg Asp Tyr
        290                 295                 300
    Lys Glu Ser Leu Cys Cys Asn Arg Pro Val Met Gly Thr Leu Arg Thr
    305                 310                 315                 320
    Asn Thr Met Leu Val Trp Glu Glu Cys Leu Asp Phe Ser Lys Thr Gln
                    325                 330                 335
    Pro Asp Leu Asn Leu Ser Ile Val Phe Phe Thr Leu Thr Leu Phe Gly
                    340                 345                 350
    Ala Pro Ile Arg Arg Cys His
                    355
```

(2) INFORMATION FOR SEQ ID NO:5:

(i) SEQUENCE CHARACTERISTICS:
        (A) LENGTH: 372 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

-continued

```
Met Ser Ser Cys Leu Gly Leu Arg Arg Ala Cys Phe Leu Leu Ser
1               5                   10                  15

Val Thr Ala Ala Ala Val Leu Leu Leu Leu Pro Arg Gly Gln Pro
                20                  25                  30

Pro Ala Pro Arg Arg Arg Pro Pro Ala Gly Pro Ser Arg Pro
            35                  40                  45

Ser Pro Lys Arg Glu Ala Arg Pro Ala Gly Ser Asp Val Pro Gly Asp
    50                  55                  60

Arg Gly Gly Gly Ser Gly Ala Ala Gly Gly Arg Gly Val Ala Gly
65                  70                  75                  80

Ser Pro Trp Pro Ser Arg Arg Val Arg Met Gly Pro Pro Gly Gly Ser
                85                  90                  95

Ala Lys Glu Ser Leu Glu Leu Lys Asp Ile Phe Ile Ala Val Lys Thr
            100                 105                 110

Thr Arg Lys Tyr His Lys Thr Arg Leu Glu Leu Leu Phe Gln Thr Trp
                115                 120                 125

Ile Ser Arg Ala Arg Gly Gln Thr Phe Ile Phe Thr Asp Trp Glu Asp
    130                 135                 140

Arg Glu Leu Arg Leu Lys Ala Gly Asp His Met Ile Asn Thr Asn Cys
145                 150                 155                 160

Ser Ala Val His Thr Arg Gln Ala Leu Cys Cys Lys Met Ser Val Glu
                165                 170                 175

Tyr Asp Lys Phe Leu Glu Ser Gly Gln Lys Trp Phe Cys His Val Asp
            180                 185                 190

Asp Asp Asn Tyr Val Asn Pro Arg Thr Leu Leu Arg Leu Leu Ser Ala
        195                 200                 205

Phe Ser Pro Ser Gln Asp Val Tyr Val Gly Arg Pro Ser Leu Asp His
    210                 215                 220

Pro Ile Glu Ala Ala Asp His Val Gln Ser Asp Gly Ser Lys Thr Ser
225                 230                 235                 240

Val Lys Phe Trp Phe Ala Thr Gly Gly Ala Gly Phe Cys Ile Ser Arg
                245                 250                 255

Gly Leu Ala Leu Lys Met Ser Pro Trp Ala Ser Leu Gly Asn Phe Ile
            260                 265                 270

Ser Thr Ala Glu Arg Val Arg Leu Pro Asp Asp Cys Thr Ile Gly Tyr
    275                 280                 285

Ile Ile Glu Gly Leu Leu Glu Val Lys Leu Leu His Ser Pro Leu Phe
290                 295                 300

His Ser His Leu Glu Asn Leu Gln Arg Leu Gln Gly Glu Ser Val Leu
305                 310                 315                 320

Gln Gln Val Thr Leu Ser Tyr Gly Asp Pro Glu Asn Lys His Asn Val
            325                 330                 335

Val Ser Val Gly Gly Val Phe Gly Leu Gln Gln Asp Pro Thr Arg Phe
                340                 345                 350

Lys Ser Val His Cys Leu Leu Tyr Pro Asp Thr Ile Trp Cys Pro Asn
            355                 360                 365

Lys Lys Met Ser
            370
```

(2) INFORMATION FOR SEQ ID NO:6:

(i) SEQUENCE CHARACTERISTICS:

(A) LENGTH: 2770 base pairs
(B) TYPE: nucleic acid
(C) STRANDEDNESS: single
(D) TOPOLOGY: linear (ix) FEATURE:
(A) NAME/KEY: CDS
(B) LOCATION: 69..1158

(xi) SEQUENCE DESCRIPTION: SEQ ID NO:6:

```
GTACATGGGC GGCCGGTGGC GGCGCGGAGC GGGGCCGGGC GGCGGAGGTG GCAGCGAGGA        60

GGAGGAGG ATG CTG AAG AGC TGC GGG AGG AAG CTG CTC CTG TCC CTC GTG        110
         Met Leu Lys Ser Cys Gly Arg Lys Leu Leu Leu Ser Leu Val
             360             365                 370

GGC TCC ATG TTC ACC TGC CTG CTG GTG CTC ATG GTG GAG CCG CCG GGC         158
Gly Ser Met Phe Thr Cys Leu Leu Val Leu Met Val Glu Pro Pro Gly
        375                 380                 385

AGG CCG GGG CTG GCT CGG GGA GAG GCC GGT GGG GCT CAG CGG GCG CTA         206
Arg Pro Gly Leu Ala Arg Gly Glu Ala Gly Gly Ala Gln Arg Ala Leu
390                 395                 400

CAG AGC CTG GGG GCG GCC CGG GCG GCG GGG CAG GGG GCT CCG GGC CTC         254
Gln Ser Leu Gly Ala Ala Arg Ala Ala Gly Gln Gly Ala Pro Gly Leu
405                 410                 415                 420

CGC ACG TTC GCC GAT TAC TTC GGG CGG CTG AGC CGG GCA CGC CGC GAG         302
Arg Thr Phe Ala Asp Tyr Phe Gly Arg Leu Ser Arg Ala Arg Arg Glu
                425                 430                 435

CTG CCC GCC GCC CCG CCG AGC CCC CCG CGG CCG CCA GCC GAG GAC ATC         350
Leu Pro Ala Ala Pro Pro Ser Pro Pro Arg Pro Pro Ala Glu Asp Ile
                440                 445                 450

ACC CCC CGC GAC GTC TTC ATC GCC GTC AAA ACC ACC AAG AAG TTC CAC         398
Thr Pro Arg Asp Val Phe Ile Ala Val Lys Thr Thr Lys Lys Phe His
                455                 460                 465

AAA GCG CGG CTG GAG CTG CTG CTC GAC ACC TGG ATC TCC CGC AAC CGC         446
Lys Ala Arg Leu Glu Leu Leu Leu Asp Thr Trp Ile Ser Arg Asn Arg
        470                 475                 480

GAC ATG ACC TTC ATC TTC ACG GAT GGG GAG GAT GAG GAG CTG AAG AAG         494
Asp Met Thr Phe Ile Phe Thr Asp Gly Glu Asp Glu Glu Leu Lys Lys
485                 490                 495                 500

CAA GCA CGA AAT GTC ATC AAC ACC AAC TGC TCG GCT GCA CAC AGC CGC         542
Gln Ala Arg Asn Val Ile Asn Thr Asn Cys Ser Ala Ala His Ser Arg
                505                 510                 515

CAG GCC CTG TCC TGC AAG ATG GCT GTG GAG TAT GAC AAG TTC ATC GAG         590
Gln Ala Leu Ser Cys Lys Met Ala Val Glu Tyr Asp Lys Phe Ile Glu
                520                 525                 530

TCT GGG AGA AAG TGG TTC TGC CAT GTG GAT GAT GAC AAC TAC GTG AAC         638
Ser Gly Arg Lys Trp Phe Cys His Val Asp Asp Asp Asn Tyr Val Asn
                535                 540                 545

GTG AGG ACG CTG GTG AAG CTG CTC TCC AGC TAT CCC CAC ACG CAG GAC         686
Val Arg Thr Leu Val Lys Leu Leu Ser Ser Tyr Pro His Thr Gln Asp
550                 555                 560

ATC TAC ATC GGG AAG CCC AGC CTG GAC AGA CCC ATC CAG GCC ACA GAG         734
Ile Tyr Ile Gly Lys Pro Ser Leu Asp Arg Pro Ile Gln Ala Thr Glu
565                 570                 575                 580

AGG ATC AGC GAG AAC AAG ATG CAC CCT GTG CAT TTC TGG TTT GCC ACG         782
Arg Ile Ser Glu Asn Lys Met His Pro Val His Phe Trp Phe Ala Thr
                585                 590                 595

GGA GGA GCA GGG TTT TGT ATC AGC CGA GGG CTG GCG CTG AAG ATG AGC         830
Gly Gly Ala Gly Phe Cys Ile Ser Arg Gly Leu Ala Leu Lys Met Ser
                600                 605                 610
```

|     |     |
| --- | --- |
| CCT TGG GCC AGT GGG GGT CAC TTC ATG AGC ACC GCG GAG AAG ATC CGC<br>Pro Trp Ala Ser Gly Gly His Phe Met Ser Thr Ala Glu Lys Ile Arg<br>     615                       620                    625 | 878 |
| CTG CCC GAT GAC TGC ACC ATT GGC TAC ATC ATC GAG TCC GTG CTG GGC<br>Leu Pro Asp Asp Cys Thr Ile Gly Tyr Ile Ile Glu Ser Val Leu Gly<br>     630                       635                    640 | 926 |
| GTG AAG CTT ATC CGC AGC AAC CTC TTC CAC TCT CAC TTG GAG AAC CTT<br>Val Lys Leu Ile Arg Ser Asn Leu Phe His Ser His Leu Glu Asn Leu<br>645                       650                    655                 660 | 974 |
| CAC CAG GTG CCC AAG ACA GAG ATC CAC AAG CAG GTG ACA CTA AGC TAT<br>His Gln Val Pro Lys Thr Glu Ile His Lys Gln Val Thr Leu Ser Tyr<br>                       665                    670                    675 | 1022 |
| GGC ATG TTT GAA AAC AAG CGC AAC TCC ATC CAC ATG AAG GGA GCC TTC<br>Gly Met Phe Glu Asn Lys Arg Asn Ser Ile His Met Lys Gly Ala Phe<br>     680                       685                    690 | 1070 |
| TCC GTG GAG GAG GAC CCA TCC AGG TTT CGC TCT GTG CAC TGC CTG CTG<br>Ser Val Glu Glu Asp Pro Ser Arg Phe Arg Ser Val His Cys Leu Leu<br>                       695                    700                    705 | 1118 |
| TAC CCC GAC ACG CCG TGG TGC CCT TCC AAC GTG GTG TAC T AGGAGACAAG<br>Tyr Pro Asp Thr Pro Trp Cys Pro Ser Asn Val Val Tyr<br>     710                       715                    720 | 1168 |
| TGTCCCCTCC CAACCTCGTC CCGAATCTCC CCGGTATCCG ACGGGTGTGC GGGACCTGCG | 1228 |
| TGCGTGCAGG TGTGTCGGTC CTCCGGACGG ACCTCGTTGC TGTGGTATTG CACAGTGTGT | 1288 |
| GTGTACTGAA GGCTGCTGTG CGGCCCTTTG TCCCCTGCCC ACCCTGCCCT GCCTGGGGAC | 1348 |
| GGCGAGCGGG GACGGGTCCT GAGCACTTAA CCCCAGGGCA TGGGGTGAGC CCCTGCCCGC | 1408 |
| CGGCAGCCCC GCGCCATGCG TGGGAGCGCA GCTCCGCGTC CCCCGCCTT GCTTTGCTTG | 1468 |
| ATTTCCTTCC AGATGTTGGT TTGTTTTTTG GTGTGTTTGC CTCCCCTCCG ACCCCCAACT | 1528 |
| CTACCCTCTT CCTCTTTCCT AGCTCCCAAA TCTCAGCATC GAGGCTCCGG CTCCTTGGTC | 1588 |
| AGGGTCACAG TTTTACACAC TCTCATTCCT CCATGGCCAC GGCAAATGCA AGCCCAGTG | 1648 |
| CCAGCATTCG CACCATTCCC CGGAGCCCCC TACATCCTGC TGAAATGTTT TCAGCGGTGT | 1708 |
| AAATCTATGC ACTATTTATA GAGACCAACT TAAAGACTTT CTATAAATAC GGGGAGAAGA | 1768 |
| GGGAGGAGGG CTTTTCCGGA GCTGTGTGTG CACAGCGCTG TGGTGTCTCC CCTGTTGTCT | 1828 |
| CCTCCTGGGC TGAGCACAGA CACCCCACAC CCTGGCACAT AGCGCTTGGG GGAGCCTTGT | 1888 |
| GGCTGTCCCC ATATCTATGG GGCTGGAACA TCCTCCTGCA GGTGGGTGCT GCTGGGGGCT | 1948 |
| GGAGCACCTG GGATGCTTGT GTGTATGTGG TGTTTCCCAA CCTGGCATTG CTCTCCGGTG | 2008 |
| CAATGGGAGA GTGATGGGCA CCCTAAAAAC ACAGGTGCCC CTCCCAAGCA CTGTCATCTG | 2068 |
| TTGTCCCATC GCTCTCCTGG GAACCTAAG AGTGGGATCC CACCTTCCCA GGTACAGCTG | 2128 |
| GAGCAAAACC AGTTTGGGAA ACGCTGCCTG GGAGCAATGT TTGCCGTGAG CCAAGGATGA | 2188 |
| ATGTAACCCA TTGCAACGAG GGTTGGGGAC TCCGTGTTCC CCATATCCCT CTCTCTGTGT | 2248 |
| CCCTTGTGGG GGGGACCAGC GGGCAGAGCT GGAGCTGAGC ATTTCCAACC CGAAGCTGAG | 2308 |
| TGAAAATGGC CCATAATGGG TGCGTTGTAC ATATGTTATT GCGCCAGTAT TTTTTTTACT | 2368 |
| GTGCCTTTTT ATAGAAAGAA AAAGAAAAAA AAAAACAAC AAGAAAGCTC AACATGGAGA | 2428 |
| ATTATGTAGA TTTTAAGATG CTTTTTATAC GTTTTCTGTG GATCGGAAAA GAAGAAAAAG | 2488 |
| ACAAACGACC TTCTGATAAT CTGTTTAAGA AAGAGAAAA GAGAAAAAAT TGCGTTGTCT | 2548 |
| TGTAACTATC ACTTACCTTA ATTTATATGT TCCAGTATCT GGAACGCCAC TCTGTGCTTT | 2608 |
| TTTGTAAGTA GGATGTGTCT CGAGGTGGTA GCTGTGGGAT GGGGAACTGG GGTGGGCAGT | 2668 |

```
GCGTTCTCAG GGACGTGAAC CCATTCACTG CCACCGTCAC CAATAAAGCA GCTTTGGGCT        2728

GACCCCCGTC CTGCAAAAAA AAAAAAAAAA AAAAAAAAAA AA                          2770
```

(2) INFORMATION FOR SEQ ID NO:7:

(i) SEQUENCE CHARACTERISTICS:
        (A) LENGTH: 363 amino acids
        (B) TYPE: amino acid
        (D) TOPOLOGY: linear (ii) MOLECULE TYPE: protein (xi) SEQUENCE DESCRIPTION: SEQ ID NO:7:

```
Met Leu Lys Ser Cys Gly Arg Lys Leu Leu Ser Leu Val Gly Ser
 1               5                  10                  15

Met Phe Thr Cys Leu Leu Val Leu Met Val Glu Pro Pro Gly Arg Pro
                20                  25                  30

Gly Leu Ala Arg Gly Glu Ala Gly Ala Gln Arg Ala Leu Gln Ser
            35                  40                  45

Leu Gly Ala Ala Arg Ala Ala Gly Gln Gly Ala Pro Gly Leu Arg Thr
    50                  55                  60

Phe Ala Asp Tyr Phe Gly Arg Leu Ser Arg Ala Arg Arg Glu Leu Pro
65                  70                  75                  80

Ala Ala Pro Pro Ser Pro Pro Arg Pro Pro Ala Glu Asp Ile Thr Pro
                85                  90                  95

Arg Asp Val Phe Ile Ala Val Lys Thr Thr Lys Lys Phe His Lys Ala
                100                 105                 110

Arg Leu Glu Leu Leu Leu Asp Thr Trp Ile Ser Arg Asn Arg Asp Met
            115                 120                 125

Thr Phe Ile Phe Thr Asp Gly Glu Asp Glu Glu Leu Lys Lys Gln Ala
130                 135                 140

Arg Asn Val Ile Asn Thr Asn Cys Ser Ala Ala His Ser Arg Gln Ala
145                 150                 155                 160

Leu Ser Cys Lys Met Ala Val Glu Tyr Asp Lys Phe Ile Glu Ser Gly
                165                 170                 175

Arg Lys Trp Phe Cys His Val Asp Asp Asp Asn Tyr Val Asn Val Arg
            180                 185                 190

Thr Leu Val Lys Leu Leu Ser Ser Tyr Pro His Thr Gln Asp Ile Tyr
    195                 200                 205

Ile Gly Lys Pro Ser Leu Asp Arg Pro Ile Gln Ala Thr Glu Arg Ile
210                 215                 220

Ser Glu Asn Lys Met His Pro Val His Phe Trp Phe Ala Thr Gly Gly
225                 230                 235                 240

Ala Gly Phe Cys Ile Ser Arg Gly Leu Ala Leu Lys Met Ser Pro Trp
                245                 250                 255

Ala Ser Gly Gly His Phe Met Ser Thr Ala Glu Lys Ile Arg Leu Pro
            260                 265                 270

Asp Asp Cys Thr Ile Gly Tyr Ile Ile Glu Ser Val Leu Gly Val Lys
    275                 280                 285

Leu Ile Arg Ser Asn Leu Phe His Ser His Leu Glu Asn Leu His Gln
290                 295                 300

Val Pro Lys Thr Glu Ile His Lys Gln Val Thr Leu Ser Tyr Gly Met
305                 310                 315                 320
```

-continued

```
Phe Glu Asn Lys Arg Asn Ser Ile His Met Lys Gly Ala Phe Ser Val
            325                 330                 335

Glu Glu Asp Pro Ser Arg Phe Arg Ser Val His Cys Leu Leu Tyr Pro
        340                 345                 350

Asp Thr Pro Trp Cys Pro Ser Asn Val Val Tyr
        355                 360
```

(2) INFORMATION FOR SEQ ID NO:8:

(i) SEQUENCE CHARACTERISTICS:
        (A) LENGTH: 3937 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
CCGGGGCGGC TTCTCACGCT AGCGGCTCGG CCCGGAGCGC CGGGCGCTGC CCTCCGCCGG    60
CCCCGGGGGC TCCGCCGCGT CCCGGAGCCG TCTGGTGGAG GCCGCGGGGG AAACCGTCCG   120
CGGGGCTCCC GGGGGCCATG AGGCTGGCCG CGCAGCGCGG CGGGGGCCGG TGGGGCCGCA   180
ACATGAGCAG CTCCTGCCTG GGCTCCGCA GAGCCTGCTT CCTGCTGTCC GTCACCGCCG   240
CCGCCGTTCT CCTGCTGCTG CTCGCCCCGG GGACAGCCCC CCGCCGCGCC CCGCCGCCGC   300
CCGCCGCCCG CCGGGCCCAG CAGGCCCTCC CCGAAGCGGG AGGCGCGGCC CGCGGGGAGC   360
GACGTGCCCG GGACCGCGG CGGCGGCTCG GGAGCCGCGG GGGCGGCCG GGCGTCGCC    420
GGTAGCCCGT GGCCTTCGCG GAGGGTCCGC ATGGGGCCTC CCGGCGGCTC GGCCAAGGAG   480
AGCCTGGAGC TAAAAGACAT CTTTATTGCG GTGAAAACGA CGAGGAAGTA TCACAAGACG   540
CGGCTGGAGC TGCTGTTCCA AACCTGGATC TCCCGGGCGA GAGGACAGAC ATTCATATTC   600
ACAGACTGGG AGGATCGAGA GCTGCGCCTG AAAGCAGGGG ATCATATGAT CAACACTAAC   660
TGTTCTGCTG TCCACACCCG GCAAGCTCTG TGCTGCAAGA TGTCTGTGGA ATATGATAAA   720
TTCCTAGAAT CTGGACAAAA GTGGTTTTGC CATGTGGACG ATGACAACTA TGTGAATCCA   780
CGGACTCTCT TGCGTCTCTT ATCTGCCTTC TCACCCAGCC AGGATGTCTA TGTGGGACGA   840
CCGAGTCTGG ACCATCCCAT TGAAGCAGCT GACCATGTCC AAAGCGATGG ATCAAAGACA   900
AGCGTGAAAT TCTGGTTTGC CACAGGTGGA GCAGGGTTCT GTATCAGCAG AGGTCTTGCT   960
CTGAAGATGA GTCCCTGGGC CAGCCTGGGT AATTTCATCA GTACTGCAGA AGAGTGCGT  1020
CTTCCTGATG ACTGCACCAT TGGCTACATC ATTGAAGGGC TGCTGGAAGT AAAGCTGCTG  1080
CACAGCCCAT TGTTCCATTC CCATCTGGAA AATCTGCAGA GACTACAAGG AGAGTCTGTG  1140
CTGCAACAGG TAACCCTAAG TTATGGGGAC CCTGAGAACA AACACAATGT TGTGAGTGTG  1200
GGAGGAGTGT TTGGACTTCA GCAAGACCCA ACCAGATTTA AATCTGTCCA TTGTCTTCTT  1260
TACCCTGACA CTATTTGGTG CCCCAATAAG AAGATGTCAT AACTTTTGAC CAGTCATTGA  1320
CACCTTTATC CTACCTACTT TGCGTAAAGC AAGAGTTGTG ATGGGCTTTT TTTCTTCTGG  1380
GACACAAACA GACATATCTA CAAAGGAGGT AGACTTTGTA CAGAAGCAAG ACTGGCTAAT  1440
TATGGCAAGA AGGCATTTGT TCAGCTGCAG CCTGGGACAT TGCCAAGAAG AAAATCTTCT  1500
ATTTCTTGTT CTTTGGTCCA GTGGCTCTTC ATGTGATGGC TCCAGTCATA GCTGTACAAG  1560
TCACTTTATG CTTTCATCTG ATGTCACATG AGCCCTGCCT ATCATGTGAA TCTGCGCTCA  1620
GATACATCCT AGGCAAATGC AGTACTTAGA ATGATGGCAT TCTTACTACT GTTAGCAGCT  1680
```

-continued

```
TTCAGAGGCC ATTGTCTTGA AGCTGGAATG TGTAAGCAGA CTGCAGTCCC CATGGTGATG    1740

AGGGGGATGA AGTTTTTGCT TGTCTTTTTT GCGAACAGGA CTTAAGAACT TCTGTGGCCT    1800

GCCATATTAT ACCTCCTCCA CCTGTGAGCT GAAACACAGT CTGTTTGTAA ACACCAGAAG    1860

TCCAGGAATT GCTAGGGTAG ACAAGGGTGA AAGCCTTTGT CATGGGAAAA ACCCTGTGTA    1920

AGGGTAAACT GACTCAGGAC TGCGCAAGAG TTGCTTACAG GGCACATTCT TCCCAGCAGT    1980

CTTTGTGTAC CTCCCATGGA GGTGATTGTC AGACTTGGCA CTCTTACCAC TGAATGGCAG    2040

TGGCTGTTGA TTATGATGGT GGTCTGCTAG GTCCAAGACT ATTCCCTTGG TATTTGATAC    2100

TGAAGATGTA TTTGCCAGAC TAGTTGGTAA CTGTTTCTCC TCCTTTCCCT CAGCAGGTTA    2160

TATGAGCTAG AGCATGCCCA TTGGCTGATG AAACACCCTG TTTTTGAAGC TGTGCTGTAT    2220

CCTTCACTGC CTGCGAGGGA GGAGGAATGC TAGATAGCTG TAGTGCTGAG AAAGGTTTTG    2280

TGGTATCATT TCAGGTCTCT TAATTGTGTG CTTGTGGTTG CCCCACTTCA GCTTCTTAAT    2340

GTAATCTTTT GAGACCAGTG TTTATTTTTA CTCTACATCT TAATGTTTCA GAAAGTAATT    2400

CTGGCACTTG GTAAAAGGAA ACTGGATGCT GATACAAAAG CAGGAGTCCA ACGCTGTAGC    2460

AATGTCACCT GCTGCGCATT ATAAATTAAA TAAGCTTAGT TTTGAAAGTG GAAGAATTGA    2520

GACTCTCTAT GTTTAGTTTT GTTACTTCCA ACTTTGCCTT TGTGCAATCT ATACCTGATG    2580

TGAAGAACAG CATACAAAAT GATTTTGTAA AACCACTGTT TACTCTCAAA CTCTTCAGAA    2640

AATACTTGCA GGTTTAGTAC TAGAGGCTGA GGCTGAATTA AGTGGAGAAT AGCATGATGT    2700

TGTATAACCT GAAACTATGA CTAATGGCGA GAATTCGGAC CGAGCAAGTT TCAGATTTCT    2760

ATCAGCTGTG CTGAGCGGTG TATTTCAGCT AGTTGCTTAA CTTCTTCCCA TTTGAAAAGT    2820

GGTACCATGT AGGCAAACAC CTGCAGCATA TTCAAGTATG AAGTGCAGTG TAGGTGTCAG    2880

CCTCCTGTAA TATAATATTC TCTGCTTTCT GTTTTTGAAG CAAACCTTTC AACAACTGGA    2940

TACGTTGTCC TCTTTGCATG ATTTAATTTA ATTTTATAGA GGAGCAAACA AGCTGACTAC    3000

TCGCTACGAT CCAGCAGCTT GTTCTTAAAT TTCTTTTCCT TTATCTGCTA AGGCAGTGCT    3060

TTGACCATGA GGCACAGGAA TAAGAGTGCT GCAAGCACTC GGATCAAAGT CCACCTAGCA    3120

CAGTGGTTGT TTCAAAACAG GAACATCTGT GATGCTGACA GCCTGTTACA GAGCGTGGAG    3180

GGCTCGTGGC AGGGTAGGTG GTGGGATGTT CTACCTCTCC ATCAGGTGGT CTGCTCAATA    3240

GAACTGAGAT GTCCTGTGGT TCAGTGATAC GTCATTCATA GCTCTGGAGA TTACTGGTAT    3300

CTATATAAAC ACTTTTTAAA AAACATTTGG TGGGTTCTTG TTTTCAGCCT CCTTGTAGCA    3360

AGGAGTTGTG AAGCTGCATA AGCACTTGAT GAGATATCAT CCTCAGTGAT CTCTGAATTC    3420

TGCTGGAGCT TTTCTTCCTC TCCTCTTAAG AGCAGCCTCC TGTCAGATAC TATGGACAGC    3480

ACAAGCTGGG TAGTGATTAT GTGGCAAACT GCAGTTCAAA GATGACAACA CTTCATACTG    3540

ATGGCAGCAA AACTGCGTAG AAGTCCCATA CTACAGTCAT TTCCCACCCT AAATGGAGTT    3600

TGCTGCCTCC TTGTCATGCC TAATGCTGGT AGGGTGCTTA TCAAGCTGAA AAAGGAACGT    3660

ATTCTTCTGT AAAGCAATGC AAAAAAGCTT CTTTAAGGTT TCTCTTGTTC ACAATACAGT    3720

AGGCTCTGTA CATATACTGA GATGCAGCTT CTTAAACTAC TGTCCCATAC GTAAAACAAT    3780

TCTATGAAAT AAATATTTAA GTATGTCAAA ACCTGGTACC CGGATCCTCG ATTCCTGCAG    3840

CCCGGGGGAT CCACTAGTTC TAGAGCGGCC GCCACCGGTG GAGCTCCAGC TTTTGTTCCC    3900

TTTAGTGAGG GTTAATTTCG AGCTTGGCGT AATCATG                            3937
```

-continued (2) INFORMATION FOR SEQ ID NO:9:

(i) SEQUENCE CHARACTERISTICS:
        (A) LENGTH: 412 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:9:

```
Met Met Ser Leu Thr Val Leu Ser Pro Pro Gln Arg Phe Lys Arg Ile
1               5                   10                  15

Leu Gln Ala Met Met Leu Ala Val Ala Val Val Tyr Met Thr Leu Leu
            20                  25                  30

Leu Tyr Gln Ser Ala Tyr Gly Tyr Pro Gly Ile Gln Val Pro His Ser
        35                  40                  45

Gln Val Asp Ala Leu Ala Ser Glu Ala Val Thr Thr His Arg Asp Gln
    50                  55                  60

Leu Leu Gln Asp Tyr Val Gln Ser Ser Thr Pro Thr Gln Pro Gly Ala
65                  70                  75                  80

Gly Ala Pro Ala Ala Ser Pro Thr Thr Val Ile Ile Arg Lys Asp Ile
                85                  90                  95

Arg Ser Phe Asn Phe Ser Asp Ile Glu Val Ser Glu Arg Pro Thr Ala
            100                 105                 110

Thr Leu Leu Thr Glu Leu Ala Arg Arg Ser Arg Asn Gly Glu Leu Leu
        115                 120                 125

Arg Asp Leu Ser Gln Arg Ala Val Thr Ala Thr Pro Gln Pro Pro Val
    130                 135                 140

Thr Glu Leu Asp Asp Ile Phe Ile Ser Val Lys Thr Thr Lys Asn Tyr
145                 150                 155                 160

His Asp Thr Arg Leu Ala Leu Ile Ile Lys Thr Trp Phe Gln Leu Ala
                165                 170                 175

Arg Asp Gln Thr Trp Phe Phe Thr Asp Thr Asp His Tyr Tyr Gln
            180                 185                 190

Glu Lys Thr Lys Gly His Leu Ile Asn Thr Lys Cys Ser Gln Gly His
        195                 200                 205

Phe Arg Lys Ala Leu Cys Cys Lys Met Ser Ala Glu Leu Asp Val Phe
    210                 215                 220

Leu Glu Ser Gly Lys Lys Trp Phe Cys His Phe Asp Asp Asn Tyr
225                 230                 235                 240

Val Asn Val Pro Arg Leu Val Lys Leu Leu Asp Glu Tyr Ser Pro Ser
                245                 250                 255

Val Asp Trp Tyr Leu Gly Lys Pro Ser Ile Ser Ser Pro Leu Glu Ile
            260                 265                 270

His Leu Asp Ser Lys Asn Thr Thr Asn Lys Lys Ile Thr Phe Trp
        275                 280                 285

Phe Ala Thr Gly Gly Ala Gly Phe Cys Leu Ser Arg Ala Leu Thr Leu
    290                 295                 300

Lys Met Leu Pro Ile Ala Gly Gly Gly Lys Phe Ile Ser Ile Gly Asp
305                 310                 315                 320

Lys Ile Arg Phe Pro Asp Asp Val Thr Met Gly Phe Ile Ile Glu His
                325                 330                 335

Leu Leu Lys Val Pro Leu Thr Val Val Asp Asn Phe His Ser His Leu
```

-continued

```
                    340                 345                 350
Glu Pro Met Glu Phe Ile Arg Gln Asp Thr Phe Gln Asp Gln Val Ser
        355                 360                 365

Phe Ser Tyr Ala His Met Lys Asn Gln Trp Asn Val Ile Lys Val Asp
        370                 375                 380

Gly Phe Asp Met Lys Thr Asp Pro Lys Arg Phe Tyr Ser Leu His Cys
385                 390                 395                 400

Gln Leu Phe Pro Tyr Phe Ser Phe Cys Pro Pro Arg
                405                 410
```